(12) United States Patent
Hoshino et al.

(10) Patent No.: US 10,980,492 B2
(45) Date of Patent: Apr. 20, 2021

(54) MAGNETIC RESONANCE IMAGING APPARATUS AND IMAGE PROCESSING APPARATUS

(71) Applicant: TOSHIBA MEDICAL SYSTEMS CORPORATION, Otawara (JP)

(72) Inventors: Tsutomu Hoshino, Palm Harbor, FL (US); Mitsue Miyazaki, Mount Prospect, IL (US)

(73) Assignee: TOSHIBA MEDICAL SYSTEMS CORPORATION, Tochigi-ken (JP)

( * ) Notice: Subject to any disclaimer, the term of this patent is extended or adjusted under 35 U.S.C. 154(b) by 1386 days.

(21) Appl. No.: 14/203,841

(22) Filed: Mar. 11, 2014

(65) Prior Publication Data

US 2014/0194730 A1    Jul. 10, 2014

Related U.S. Application Data

(63) Continuation-in-part of application No. 13/470,052, filed on May 11, 2012, now Pat. No. 8,855,743.

(30) Foreign Application Priority Data

May 10, 2013    (JP) .............................. JP2013-100719

(51) Int. Cl.
  *A61B 5/00*    (2006.01)
  *A61B 5/055*   (2006.01)
  *G01R 33/563*  (2006.01)
(52) U.S. Cl.
  CPC ............ *A61B 5/743* (2013.01); *A61B 5/0044* (2013.01); *A61B 5/055* (2013.01); *G01R 33/56366* (2013.01); *A61B 5/7285* (2013.01)

(58) Field of Classification Search
  CPC .................................................. G01R 33/563
  See application file for complete search history.

(56) References Cited

U.S. PATENT DOCUMENTS

| | | | |
|---|---|---|---|
| 6,442,414 B1 * | 8/2002 | Watanabe | .............. A61B 5/055 324/306 |
| 6,498,946 B1 | 12/2002 | Foo et al. | |
| 6,564,080 B1 | 5/2003 | Kimura | |
| 7,328,054 B2 | 2/2008 | Jesmanowicz | |

(Continued)

FOREIGN PATENT DOCUMENTS

| | | |
|---|---|---|
| JP | 10-328158 | 12/1998 |
| JP | 2000-342555 | 12/2000 |

(Continued)

OTHER PUBLICATIONS

Office Action dated Sep. 7, 2015 in CN 201380003460.3.

(Continued)

*Primary Examiner* — Jason M Ip
(74) *Attorney, Agent, or Firm* — Nixon & Vanderhye, P.C.

(57) ABSTRACT

A magnetic resonance imaging (MRI) apparatus according to an exemplary embodiment includes a sequence controller and a data processor. The sequence controller executes a pulse sequence using a combination of multiple types of labeling methods to acquire magnetic resonance signals. The data processor generates multiple types of labeled images based on the magnetic resonance signals.

17 Claims, 18 Drawing Sheets

(56) References Cited

U.S. PATENT DOCUMENTS

| | | | |
|---|---|---|---|
| 2005/0033159 A1* | 2/2005 | Mistretta | G01R 33/563 600/420 |
| 2008/0238422 A1* | 10/2008 | Yui | G01R 33/4824 324/307 |
| 2011/0071382 A1 | 3/2011 | Miyazaki et al. | |
| 2011/0080170 A1 | 4/2011 | Miyazaki | |

FOREIGN PATENT DOCUMENTS

| | | |
|---|---|---|
| JP | 2007-190114 | 8/2007 |
| JP | 2009-261421 | 11/2009 |
| JP | 2011-083592 | 4/2011 |
| WO | 00/065995 A1 | 11/2000 |

OTHER PUBLICATIONS

Zun, et al., "Assessment of Myocardial Blood Flow (MBF) in Humans Using Arterial Spin Labeling (ASL) Feasibility and Noise Analysis," *Magnetic Resonance in Medicine*, vol. 62, pp. 975-983 (2009).

International Search Report dated Aug. 13, 2013 in PCT/JP2013/063214.

Mitsue Miyazaki et al., "Nonenhanced MR Angiography," Radiology, Jul. 2008, vol. 248, No. 1, pp. 20-43.

M. Katoh et al., "Flow Targeted Coronary MR Angiography: Comparison of Three Different Spin Labeling Techniques," Proc. Intl. Soc. Mag. Reson. Med. 13, May 2005, p. 709.

Y. Wang et al, "High Resolution 3D MR Angiography using Arterial Spin Labeling," Proc. Intl. Soc. Mag. Reson. Med. 17, Apr. 2009, p. 94.

Office Action for U.S. Appl. No. 13/470,052 dated Jun. 26, 2013.

* cited by examiner (TYPE A)

(TYPE B)

(TYPE C)

(TYPE D)

FIG.9
(A) 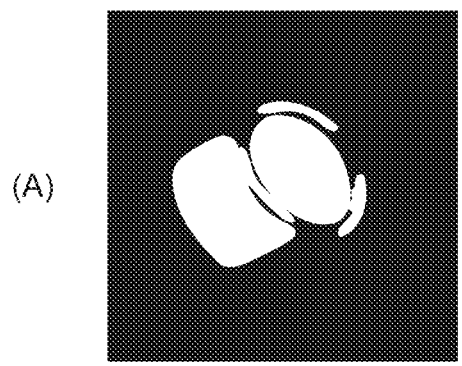
|A-B|
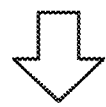
(B) 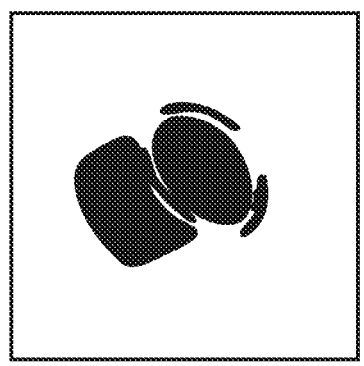
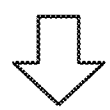
(C) 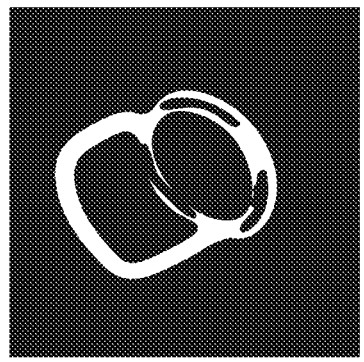

FIG.10
(A)
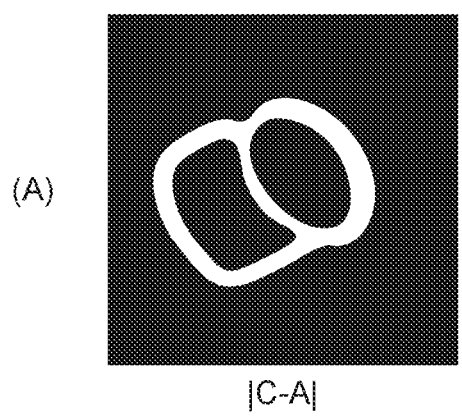
|C-A|
(B)
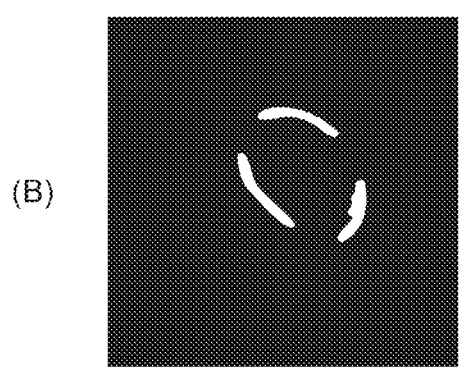

SHORT-AXIS VIEW

MAGNETIC RESONANCE IMAGING APPARATUS AND IMAGE PROCESSING APPARATUS

CROSS-REFERENCE TO RELATED APPLICATIONS

This application is a continuation-in-part (CIP) of application Ser. No. 13/470,052 filed on May 11, 2012 (now U.S. Pat. No. 8,855,743 issued Oct. 7, 2014), the entire content of which is hereby incorporated by reference in this application. This application is based upon and claims the benefit of priority from Japanese Patent Application No. 2013-100719, filed on May 10, 2013, the entire contents of all of which is incorporated herein by reference.

FIELD

Exemplary embodiments relate to a magnetic resonance imaging apparatus and an imaging processing apparatus.

BACKGROUND

Magnetic resonance imaging is an imaging method in which nuclei of a patient placed within a static magnetic field are magnetically excited by a high frequency (RF(radio frequency)) signal of the Larmor frequency and an image is reconstructed from magnetic resonance (MR) signals generated in accordance with the excitation. In the field of magnetic resonance imaging, non-contrast MRA (Magnetic Resonance Angiography) is known as a method of acquiring images of blood vessels without using a contrast agent.

BRIEF DESCRIPTION OF THE DRAWINGS

FIG. 9 illustrates image processing according to the embodiment;
FIG. 10 illustrates image processing according to the embodiment.

DETAILED DESCRIPTION

A magnetic resonance imaging(MRI) apparatus according to an exemplary embodiment includes a sequence controller and a data processor. The sequence controller executes a pulse sequence using a combination of multiple types of labeling methods to acquire magnetic resonance signals. The data processor generates multiple types of labeled images based on the magnetic resonance signals.

Exemplary embodiments of myocardial perfusion imaging (MPI) using ASL (arterial spin labeling) will be described below. In the exemplary embodiments, an MRI system 100 generates a myocardial perfusion image based on a non-contrast cardiac image acquired by using a combination of labeling pulses. The MRI system 100 allows users to easily understand the cardiac information on, for example, myocardium and blood perfusion and displays MR images using a supporting method to check a region of ischemia or a region of infarction.

Figure 1:
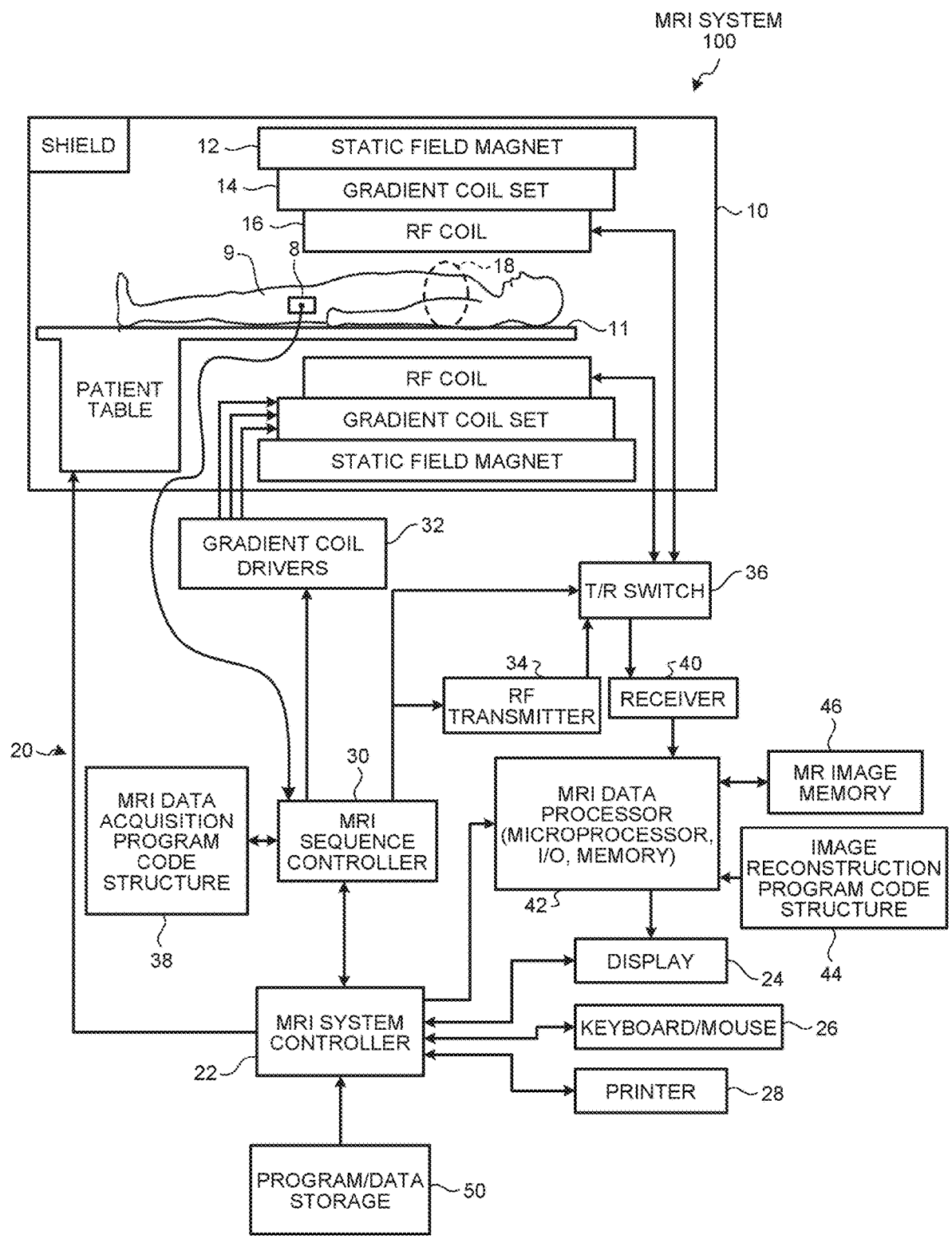
FIG. 1 is a schematic block diagram of an MRI system according to an embodiment.

FIG. 1 is a schematic block diagram of the MRI system 100 according to an embodiment. The MRI system 100 shown in FIG. 1 includes a gantry 10 (shown in schematic cross-section) and various related system components 20 interfaced therewith. At least the gantry 10 is typically located in a shielded room. The gantry 10 depicted in FIG. 1 includes a substantially coaxial cylindrical arrangement of a static field magnet 12 ($B_o$), gradient coil set 14 ($G_x$, $G_y$ and $G_z$) and an RF coil 16. Along the horizontal axis of this coaxial cylindrical array of elements, is an imaging volume 18 shown as substantially encompassing the heart tissue of a patient 9 supported by a patient table 11.

An MRI system controller 22 has input/output ports connected to a display 24, a keyboard/mouse 26 and a printer 28. As will be appreciated, the display 24 may be of the touch-screen variety so that it provides control inputs as well.

The MRI system controller 22 interfaces with MRI sequence controller 30 which, in turn, controls gradient coil drivers 32, as well as an RF transmitter 34 and a transmit/receive switch 36 (if the same RF coil is used for both transmission and reception). Additional body "surface" RF coils (perhaps in arrayed dispositions) may also be used for RF coupling to selected regions as will be understood. As those skilled in the art will appreciate, one or more electrodes 8 may be affixed to the patient's body to provide ECG (electrocardiogram), respiratory and/or pulse wave signals to the MRI sequence controller 30. The MRI sequence controller 30 also has access to a suitable program code structure 38 for executing an effective pulse sequence to generate non-contrast MRA images and/or non-contrast MRV (magnetic Resonance Venography) images and/or blood perfusion images using operator and/or system inputs defining particular pulse sequence parameters.

The system components 20 include an RF receiver 40 providing input to an MRI data processor 42 so as to create processed image data that may be output to the display 24. The MRI data processor 42 is also configured for access to an image reconstruction program code structure 44 and to an MR image memory 46 (e.g., for storing MR image data derived from processing in accordance with the exemplary embodiments and the image reconstruction program code structure 44).

FIG. 1 provides generalized description of a program/data store 50. The program code structures (e.g., program code structures for Time-SLIP (Spatial Labeling Inversion Pulse) image acquisition, image processing and display of mpm-contrast cardiac perfusion imaging, operator inputs to same, etc.) stored in the MRI system program/data store 50 are stored in computer readable memory media accessible to the various data processing components of the MRI system 100. As those in the art will appreciate, the program/data store 50 may be segmented and directly connected, at least in part, to different ones of the system components 20 having most immediate need for such stored program code structures in their normal operation (i.e., rather than being commonly stored and connected directly to the MRI system controller 22).

Indeed, as those skilled in the art will appreciate, the FIG. 1 depiction is a very high-level simplified diagram of a typical MRI system with some modifications so as to practice exemplary embodiments to be described hereinbelow. The system components can be divided into different logical collections of "boxes" and typically include numerous digital signal processors (DSP), microprocessors, special purpose processing circuits (e.g., for fast A/D conversions, fast Fourier transforming, array processing, etc.). Each of those processors is typically a clocked "state machine" wherein the physical data processing circuits progress from one physical state to another upon the occurrence of each clock cycle (or predetermined number of clock cycles).

Not only does the physical state of processing circuits (e.g., CPUs (Central Processing Unit), registers, buffers, arithmetic units, etc.) progressively change from one clock cycle to another during the course of operation, the physical state of associated data memory media (e.g., bit memory sites in magnetic memory media) is transformed from one state to another during operation of such a system. For example, at the conclusion of an MR imaging reconstruction process, an array of computer-readable accessible data value memory sites in physical memory media will be transformed from some prior state (e.g., all uniform "zero" values or all "one" values) to a new state wherein the physical states at the physical sites of such an array vary between minimum and maximum values to represent real-world physical events and conditions (e.g., the tissues of a patient over an imaged volume space). As those in the art will appreciate, such arrays of stored data values represent and also constitute a physical structure—as does a particular structure of computer control program codes that, when sequentially loaded into instruction registers and executed by one or more CPUs of the MRI system 100, cause a particular sequence of operational states to occur and be transitioned through within the MRI system 100.

The exemplary embodiments described below provide improved ways to acquire and/or process data and/or to generate and display MR images.

Non-contrast MRA techniques include the Time-SLIP technique. The Time-SLIP technique labels a fluid flowing into or flowing out of a region to be imaged (imaged region) in a region to be labeled (labeled region) independent of the image area. The labeled region is set in, for example, an upstream region on the route for the fluid. Accordingly, the fluid flowing out of or flowing into the imaged region when a predetermined time has passed is imaged with a relatively high signal value (imaged brightly) or with a low signal value (imaged darkly).

The Time-SLIP technique applies a non-selective IR (Inversion Recovery) pulse and a selective IR pulse almost simultaneously when a predetermined time has passed since a trigger signal. A non-selective IR pulse is an IR pulse applied without selecting a region. On the other hand, a selective IR pulse is an IR pulse applied to the labeled region. Choices on whether to apply non-selective and/or selective IR pulses can be appropriately combined.

A typical example will be described here. If a labeled region is created within an imaged region and the MRI system 100 applies a non-selective IR pulse, longitudinal magnetization components of the tissue over the imaged region are accordingly inverted. The MRI system 100 then applies a selective IR pulse only to the labeled region in the imaged region and accordingly the longitudinal magnetic components in the labeled region are inverted again. The longitudinal magnetic components of the tissue to which only the non-selective pulse has been applied gradually recover. Accordingly, when a predetermined time has elapsed (e.g., at a null point), a statistically significant difference occurs between the longitudinal magnetic components of the labeled tissue and the longitudinal magnetic components of other tissues and thus only the fluid that is labeled in the labeled region can be visualized with the relatively high signal values. The predetermined time may be referred to as BBTI (Black-Blood Time to Inverse). Because the labeled fluid flows out of the labeled region into the imaged region, it may be referred to as, for example, a "flow-out".

On the other hand, if a labeled region is set outside a region to be imaged and the MRI system 100 applies a selective IR pulse to only the labeled region outside the imaged region, longitudinal magnetic components of the tissue in the labeled region are inverted. The fluid that is labeled in the labeled region then flows into the imaged region. Because no IR pulse has been applied to the tissue in the imaged region, a significant difference occurs between the longitudinal magnetic components of the labeled fluid and the longitudinal magnetic components of the tissue in the imaged region and, accordingly, only the fluid that is labeled in the labeled region can be visualized with a relatively low signal value. Because the labeled fluid flows into the imaged region, it may be referred to as, for example, a "flow-in".

The position of the labeled region, a combination of IR pulses, and names thereof can be changed as required.

However, using Time-SLIP acquisition has encountered disadvantages such as the following:

In one teaching, 2D acquisition scans (i.e., where a slice is imaged using 2D Fourier Transformation based on acquired data that incorporates 2D phase encoding) has been used with no time adjustment of the flowing blood period. Not only was the observation area limited to a single slice due to a single 2D acquisition process; but, in addition, although blood travel time varies with each individual, only a single transit time (i.e., one BBTI) was.

In other approaches, two separate (i.e., over two respectively corresponding breath-hold periods) 2D or 3D acquisition scans (i.e., where 3D acquisition scanning is performed in a relatively longer acquisition process incorporating 3D phase encoding) were used with the labeling on respectively corresponding acquisitions, causing misregistration and making it difficult to subtract the images without having significant registration errors.

Figure 2:
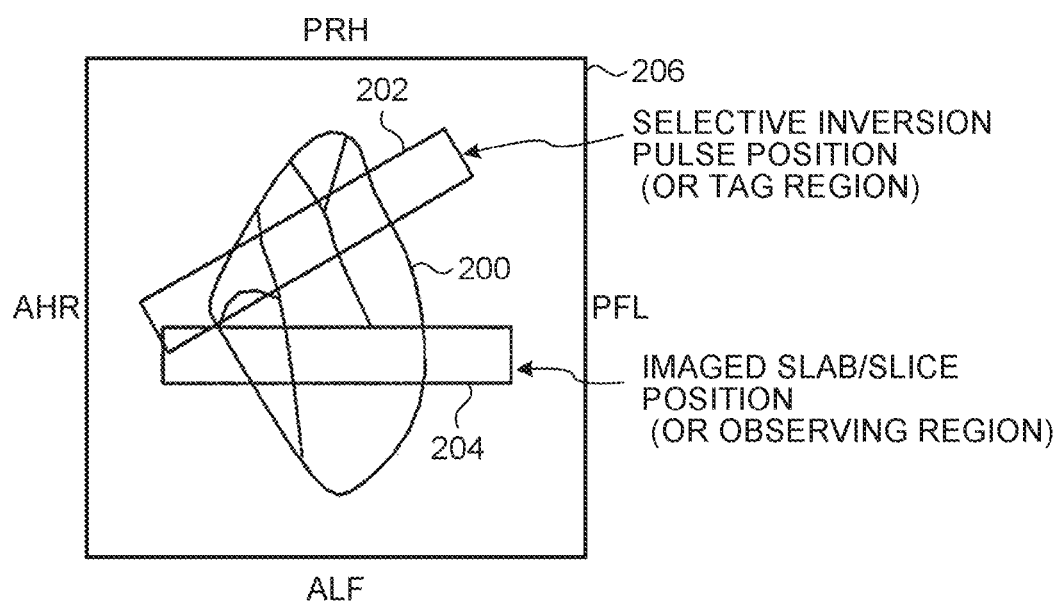
FIG. 2 is a depiction of a scout planning image according to an exemplary embodiment.

A scout planning image is schematically depicted in FIG. 2. Here, A stands for anterior, P for posterior, H for head, F for foot, R for right and L for left. In MRI, MR images can be acquired with oblique angles, which means that one side of the images may correspond to Anterior, Head and Right-hand side at the same time, and are thus tagged as AHR. Of course, the other side of the image must be PFL in this case.

A non-selective IR pulse is applied to an entire volume 206 and a selective IR pulse is applied to an upstream volume 202 (e.g., above a cardiac tissue 200 of interest). 3D MRI data is then acquired for an imaged volume 204.

As will be explained in more detail below, multiple 3D MRI data sets are acquired in one breath-hold period to reduce misregistration during subsequent inter-image data processing on MR images.

The MRI system 100 acquires multiple types of labeled images with reduced misregistration executing a pulse sequence using a combination of multiple types of labeling methods. The MRI system 100 generates analyzed images by, for example, perform& performing a subtraction operation between images and displays the generated analyzed images effectively. Specifically, the MRI sequence controller 30 executes a pulse sequence using a combination of multiple types of labeling methods. For such multiple types of labeling methods, four labeling methods can be used each defining whether to apply a "non-selective IR pulse", which is a labeling pulse applied without a region to apply a pulse being selected, and/or apply a "selective IR pulse", which is a labeling pulse applied with a region to apply a pulse being selected.

FIGS. 3 to 6 illustrate labeling methods of the embodiment. Multiple types of labeling methods include the following types:

a first method where a non-selective IR pulse is applied but no selective IR pulse is applied, a second method where a non-selective IR pulse and a selective IR pulse are applied almost simultaneously, a third method where no non-selective IR pulse is applied but a selective IR pulse is applied, and a fourth method where neither non-selective IR pulse nor selective IR pulse is applied. Note that the fourth method is described as a labeling method although it applies no labeling pulse.

FIGS. 3, 4, 5 and 6 illustrate the first, second, third and fourth methods, respectively. The waiting time after application of a non-selective pulse until MR signals are acquired can be referred to as "BBTI". Even for the labeling method where no non-selective IR pulse is applied, the waiting time after the time when a non-selective IR pulse is assumed to be applied until acquisition of MR signals is started is referred to as BBTI.

Figure 7A:
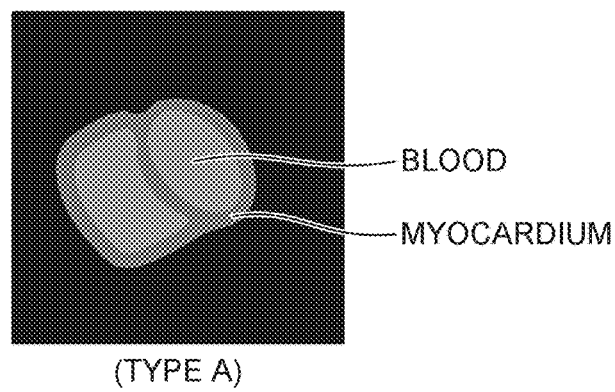
FIG. 7A is an exemplary labeled image generated by a labeling method according to the embodiment.
Figure 7B:
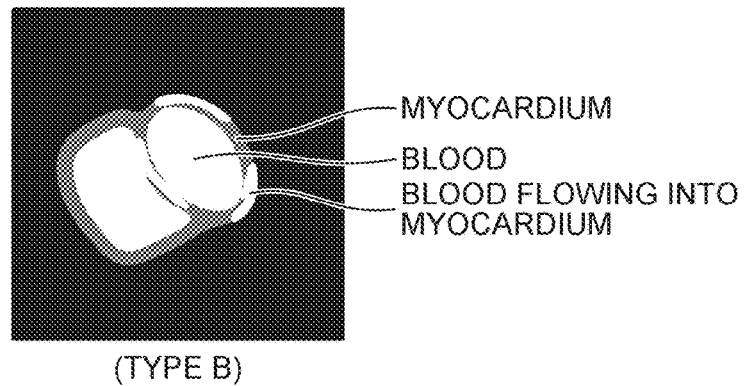
FIG. 7B is an exemplary labeled image generated by a labeling method according to the embodiment.
Figure 7C:
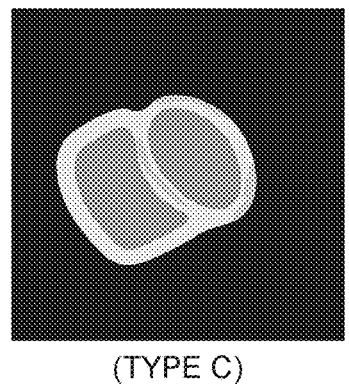
FIG. 7C is an exemplary labeled image generated by a labeling method according to the embodiment.
Figure 7D:
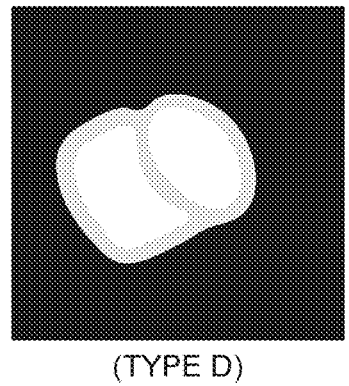
FIG. 7D is an exemplary labeled image generated by a labeling method according to the embodiment.

FIGS. 7A to 7D are exemplary labeled images acquired using the respective labeling methods of the embodiment. FIG. 7A is an exemplary labeled image that is generated based on MR signals that are acquired using the first method. The labeled image is referred to as a "Type-A" labeled image. FIG. 7B is an exemplary labeled image that is generated based o MR signals acquired using the second method. The labeled image is referred to as a "Type-B" labeled image. FIG. 7C is an exemplary labeled image that is generated based on MR signals acquired using the third method. The labeled image is referred to as a "Type C" labeled image. FIG. 7D is an exemplary labeled image that is generated based on MR signals acquired using the fourth method. The labeled image is referred to as a "Type D" labeled image.

The labeled images of FIGS. 7A to 7D are all simplified short axis views. If the difference between the signal value of myocardium and that of blood is small, some signal differences cannot be seen well in FIGS. 7A to 7D, but every drawing contains the relationship between relative signal values that are organized in Table 1 to be shown below. For example, as shown in FIG. 7A, the myocardium and the blood remaining in the myocardium are imaged in a short axis view. As shown in FIG. 7B, when a selective IR pulse is applied, the blood flowing into the myocardium is imaged with, for example, a higher signal value in a short axis view. As shown in FIG. 7C, when no non-selective IR pulse is applied and a selective IR pulse is applied, the blood flowing into the myocardium is imaged with, for example, a lower signal value in a short axis view. The signal value of blood has a smaller contribution compared to that of the myocardium, which makes it difficult to see the blood flowing into the myocardium. The fundamental relationship between the signal values of signals in labeled images and the labeling methods is organized in Table 1 below, where "−" indicates a relatively low signal value and "+" indicates a relatively high signal value.

TABLE 1

| | First method (Type A) Non-selective: Yes Selective: No | Second method (Type B) Non-selective: Yes Selective: Yes | Third method (Type C) Non-selective: No Selective: Yes | Fourth method (Type D) Non-selective: No Selective: No |
|---|---|---|---|---|
| Blood | − | + | − | + |
| Myocardium | − | − | + | + |

The MRI sequence controller 30 of the embodiment uses a combination of the multiple types of labeling methods in a single breath-hold period to acquire all MR signals corresponding to multiple types of volume data (or multi slice data) in a single breath-hold. This reduces misregistration between multiple types of volume data (or multiple types of multi slice data) and as a result increases the accuracy of a desired image that is acquired by, for example, performing a subtraction operation between multiple types of labeled images.

An example will be described below in which the MRI sequence controller 30 acquire a type-A labeled image and a type-B labeled image by using a combination of the first and second methods in one breath-hold period while changing the BBTI for each breath-hold period.

Figure 8:
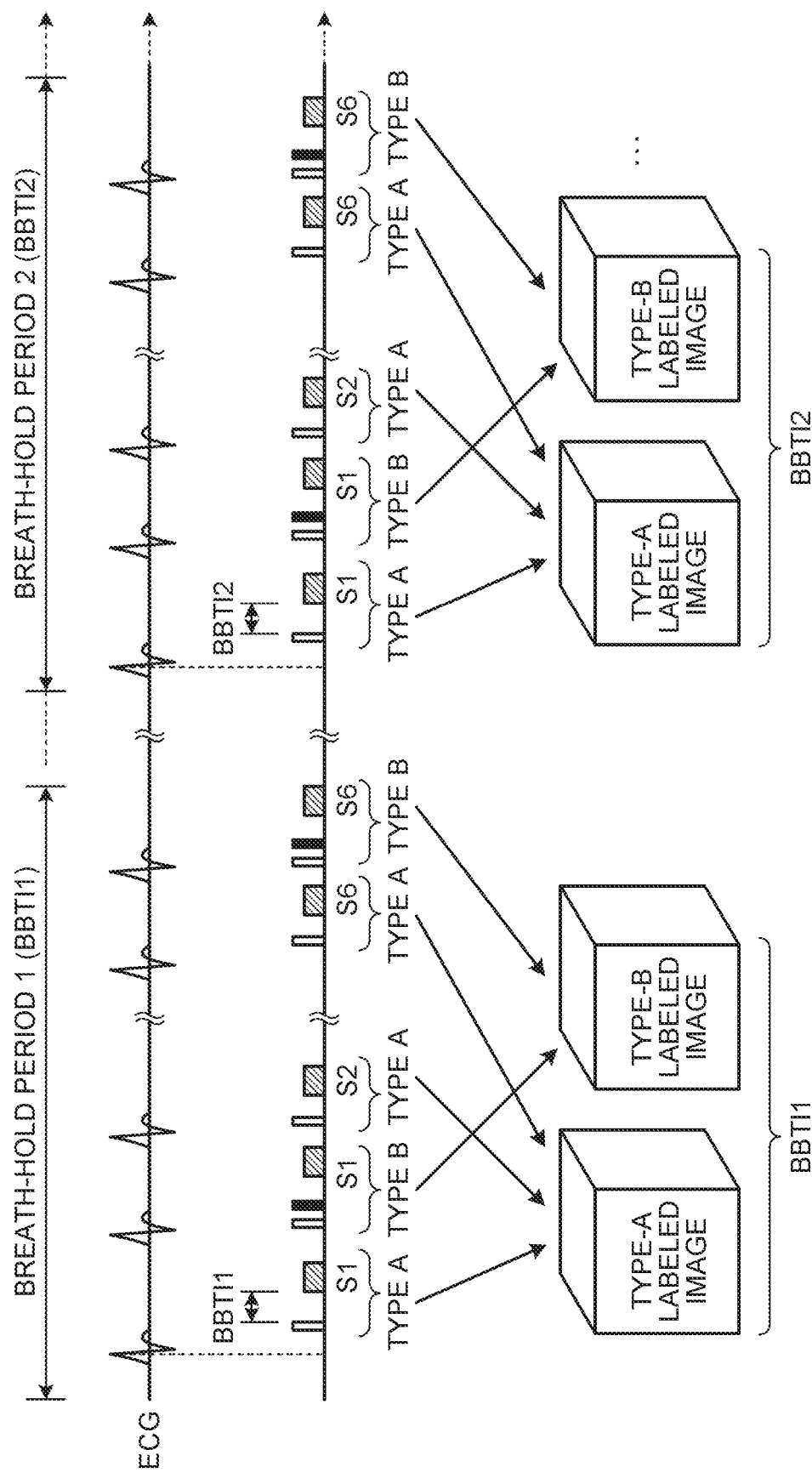
FIG. 8 depicts an execution of a pulse sequence according to the embodiment.

FIG. 8 depicts execution of a pulse sequence of the embodiment. Although FIG. 8 simply depicts a breath-hold period 1 and a breath-hold period 2 of different BBTI, Execution of a pulse sequence is typically uninterruptedly continued after the breath-hold period 3 and the following period, with the BBTI being changed. When 3D volume data is acquired over the pulse sequence in FIG. 8, "S1" and "S2" correspond to "slice encode 1" and "slice encode 2", respectively. In contrast, when 2D multi slice data is acquired over the pulse sequence in FIG. 8, "S1" and "S2" correspond to "slice 1" and "slice 2", respectively.

For example, the MRI sequence controller 30 acquires all MR signals corresponding to "S1" to "S6" while alternately repeating acquisition using the first method and acquisition using the second method over one breath-hold period (for example, approximately 18 seconds). The MRI sequence controller 30 uses an ECG signal (for example, R wave) of the patient as a trigger signal. The MRI sequence controller 30 applies a non-selective IR pulse when a predetermined time has passed since the trigger signal and then acquires MR signals when a BBTI1 has passed since an application of the non-selective IR pulse. Accordingly, a type-A labeled image for at least 1 slice encode (1 slice) corresponding to BBTI1 is acquired.

The MRI sequence controller 30 uses an ECG signal (for example, R wave) of the patient as a trigger signal. When a predetermined time has passed since the trigger signal, the MRI sequence controller 30 applies a non-selective IR pulse and, almost simultaneously, applies a non-selective IR pulse. Furthermore, when a BBTI1 has elapsed, the MRI sequence controller 30 acquires MR signals. Accordingly, a type-B labeled image for at least 1 slice encode (1 slice) corresponding to BBTI1 is acquired. As described above, the MRI sequence controller 30 alternately repeats acquisition of type-A labeled image and acquisition of type-B labeled image to acquire type-A labeled images and type-B labeled images of 1 volume data in a single breath-hold period.

The MRI sequence controller 30 changes the BBTI from BBTI1 to BBTI2 and then again acquires all MR signals corresponding to "S1" to "S6" while alternately repeating acquisition using the first method and acquisition using the second method over a single breath-hold. Thus, type-A labeled images and type-B labeled images of 1 volume data are acquired over a single breath-hold period.

The number of seconds of a breath-hold period, the number of slice encodes, the number of slices, etc, can be changed arbitrarily. The technique is not limited to that where acquisition using the first method and that using the second method are alternately repeated. For example, acquisition according to the second method may be performed over "S1" to "S6" after acquisition using the first method is performed over "S1" to "S6". According to the example of FIG. 8, a single breath-hold period acquisition includes both "non-selective IR pulse alone" and " both non-selective and selective IR pulses", where each slice or slice encoding (actual imaging or read-out) is triggered at the same cardiac phase, preferably diastole. Repetitions of this process using different BBTIs can be executed to observe the time course of marked (e.g., "tagged") blood travel into the myocardium.

In order to understand the period of blood travel time from the marked (or equivalently, tagged or labeled) region to the myocardium region of interest, a series of 2D acquisitions can be performed using different BBTIs triggered at the same cardiac phases in a breath-hold period or using one 2D Time-SLIP acquisition with bSSFP (balanced Steady-State Free Precession) (or FFE (Fast Field Echo)) segmented cine to provide a rough estimation of marked blood perfusion timing (meaning when blood supplies arrive at the myocardium).

Figure 3:
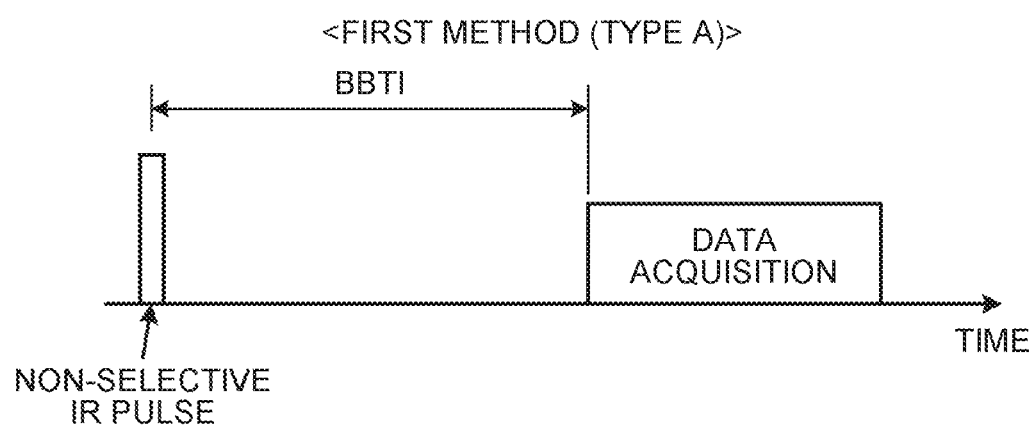
FIG. 3 illustrates a labeling method according to the embodiment.
Figure 4:
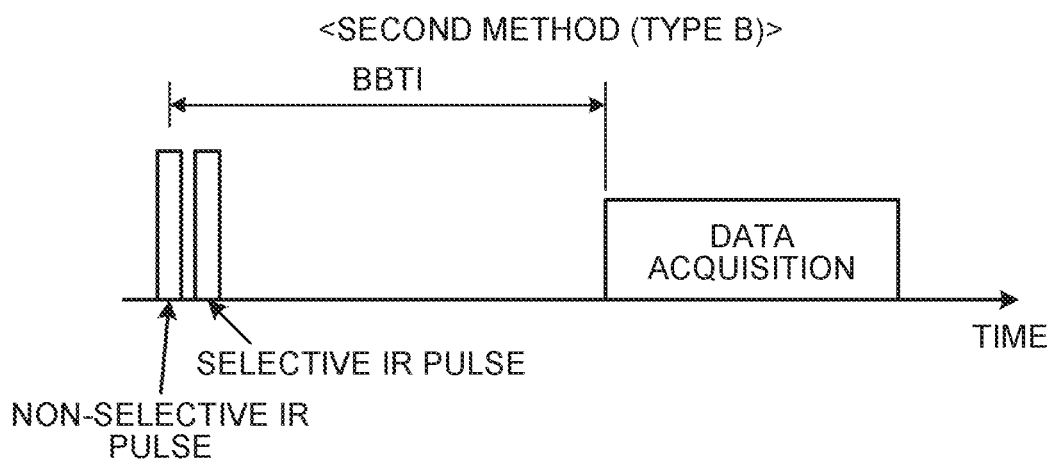
FIG. 4 illustrates a labeling method according to the embodiment.

The non-selective IR pulse reduces the signal values of myocardium and blood flowing into the heart. If this pulse is used alone, both blood and myocardium will experience T1 recovery during imaging (FIG. 3, type A). If a selective IR pulse is also applied in an upstream region for the heart immediately after the non-selective IR pulse, then the blood signal is restored (i.e., tagged) before coming into the heart and the tagged blood will be imaged as bright pixels (FIG. 4, type B). A time constant, BBTI, controls the time in which the tagged blood is allowed to enter the heart, as well as how much T1 recovery the myocardium will have. By acquiring these two sets of images within one breath-hold period to minimize registration errors, blood contributions to the MRI signal can be isolated from myocardium by subtracting one image from the other (using complex-valued pixel-by-pixel image subtraction processes).

This aspect will be described more in detail. The MRI data processor 42 generates multiple types of labeled images based on the MR signals that are acquired by the MRI sequence controller 30 and performs a subtraction operation between multiple types of labeled images, thereby acquiring desired images. The desired images are used for, for example, easily finding a region of ischemia or myocardial infarction. Different from normal myocardium, no (or little) blood flow is observed in a region of ischemia or myocardial infarction. The MRI data processor 42 performs, in addition to a subtraction operation, threshold and pixel-value inversion operations to image regions where no (little) blood flow is observed.

The processes performed by the MRI data processor 42 to generate desired images assuming that the MRI sequence controller 30 acquires both type-A and type-B labeled images will be described.

The MRI data processor 42 uses type-A labeled images and type-B labeled images of the same BBTI to calculate the pixel value Ii at pixel location i for each slice as:

$$I_i = (\theta_0 - \min(\theta_0, |A_i - B_i|)) F(\max(|A_i|, |B_i|), T_{BBTI}) \quad (1)$$

where $A_i$ and $B_i$ are complex numbers representing pixel values at pixel location i of a type A image and of a type B image, respectively, and $\theta_0$ is a threshold value. The subscript i in $I_i$ of Equation (1) is a shorthand notation for a pixel location (x,y) in an image. $\theta_0$ is a constant threshold value (over BBTI) that is to be adjusted based on the image for a given set of scan parameters. Once determined, the constant threshold can be used for all patients. However, it is possible to let the user choose $\theta_0$ for each BBTI in order to change sensitivity to the difference between type A and type B depending on BBTI. In this case, $\theta_0$ is no longer a constant over BBTI. In order to prevent non-signal regions from being brightly imaged, a continuous threshold function of $|A_i|$, $|B_i|$, and BBTI is multiplied by function F. The dependency of BBTI is needed to compensate signal changes based on the T1 recovery of the tissue. An example of the function F is a sigmoid function like $$F(x, t) = \left( \frac{1}{1 + \exp\left(-\frac{x - g(t)}{6g(t)}\right)} \right) \quad (2)$$

where g(t) is a function that represents threshold changes depending on BBTI. An example of g(t) is one that takes into account the T1 recovery. F(x, t) is a sigmoid function whose value monolithically increases from 0 to 1. t determines where the value becomes 0.5. More precisely, when x=g(t), F(x, t) becomes 0.5. In this sense, g(t) is a threshold value and it changes depending on t. The function F masks out areas whose signal intensity is very small because:

1. the reverse intensity operation make areas bright where there are very small signal differences between type-A and type-B images;

2. this also includes areas where both signals of A-type and B-type labeled images are very small from the beginning (e.g., air); and 3. F(x, t) makes these areas dark due to its smooth threshold operation.

$$g(t) = C\max\left(\varepsilon, \left|1 - 2\exp\left(-\frac{t}{T_1}\right)\right|\right) \quad (3)$$

where C and ε are parameters to be adjusted and T1 is the T1 recovery constant of myocardium, which is around 1,000 to 1,200 ms. C in the definition of g(t) in Equation (3) is a constant (over BBTI) and can be determined empirically. One way is to adjust C so as to make g(BBTI) equal to the average myocardium signal in the region of interest. ε is simply a small number chosen so as to avoid possible attempted division by zero (for example, 0.01).

This image processing will be described more in detail. FIG. 9 illustrates the image processing of the embodiment. As indicated by "$A_i$–$B_i$" in Equation (1), the MRI data processor 42 performs a subtraction operation between type-A and type-B labeled images. The reason for performing a subtraction operation in complex numbers will be described. The magnetization vectors of nuclei are represented as real components (coordinate phase components) and imaginary components (quadrature phase) on the complex plane. Thus, MRI acquires k-space data of each of real number components and imaginary number components, generates a real number image and an imaginary number image according to Fourier transform, and then generates an amplitude image, which is an absolute value image and a phase image.

As described above, a type-A labeled image and a type-B labeled image are different in that whether a non-selective IR pulse is applied. The difference appears as the difference in longitudinal magnetization components. However, it appears as the difference of phases in transverse magnetization components on the xy plane after application of excitation pulse. This is because, for example, the phase varies between when the upward magnetization vector tips to the xy plane and when the downward magnetization vector inclines toward the xy plane. To correctly take the phase difference into account, the MRI data processor 42 performs a subtraction operation using complex numbers.

As indicated by "|$a_i$–$B_i$|", the MRI data processor 42 calculates an absolute value of the image on which the subtraction operation using complex numbers has been performed. In the absolute value image, as FIG. 9(A) shows, the signal value of pixels for a location where blood exists is high (bright) and the signal value of pixels of other locations is low (dark). As described above, desired images of the embodiment are images for easily finding a region of ischemia or myocardial infarction. It is more preferable that the signal value of pixels for a location where no blood exists be high (bright).

As indicated by "($\theta_0$−min($\theta_0$, |$A_i$−$B_i$|))", the MRI data processor 42 performs inversion processing on signal values using threshold processing. The MRI data processor 42 compares the image signal values |$A_i$−$B_i$| to the threshold $\theta_0$, changes all signal values of pixels larger than the threshold $\theta_0$ to $\theta_0$, and performs a subtraction operation using $\theta_0$ to change all signal values to 0. As a result, an image shown in FIG. 9(B) with brightness inverted with respect to that of the image of FIG. 9(A) is obtained. In the image of FIG. 9(B), pixels whose signal value difference is small between the type-A and type-B labeled images, i.e., pixels for a location where no blood exists, have high signal values (bright).

In the image of FIG. 9(B), the pixels for regions excluding myocardium, e.g., air, have high signal values (bright). Thus, as indicated by "F(max(|$I_i$|, |$B_i$|), $T_{BBTI}$)", the MRI data processor 42 performs a threshold operation using a function F. Specifically, the MRI data processor 42 increases the pixel signal value (makes the pixel bright) if the higher signal value of "$A_i$" and "$B_i$" exceeds a threshold and reduces the signal value of other pixels (makes the pixel dark). This leads to an image where, as in FIG. 9(C), the region of myocardium is bright and the region of the air is dark and the region of myocardium the blood has not reached is bright and the region the blood has reached is dark.

The process to generate a desired image has been described above assuming that labeling images of both type-A and type-B had been acquired. However, this does not limit the scope of embodiments. If a different combination of labeled images is acquired, image processing appropriate to the combination is performed appropriately to generate a desired image.

Another exemplary case will be described where type-A volume data, type-B volume data, and type-C volume data are acquired in one breath-hold period, respectively.

Figure 5:
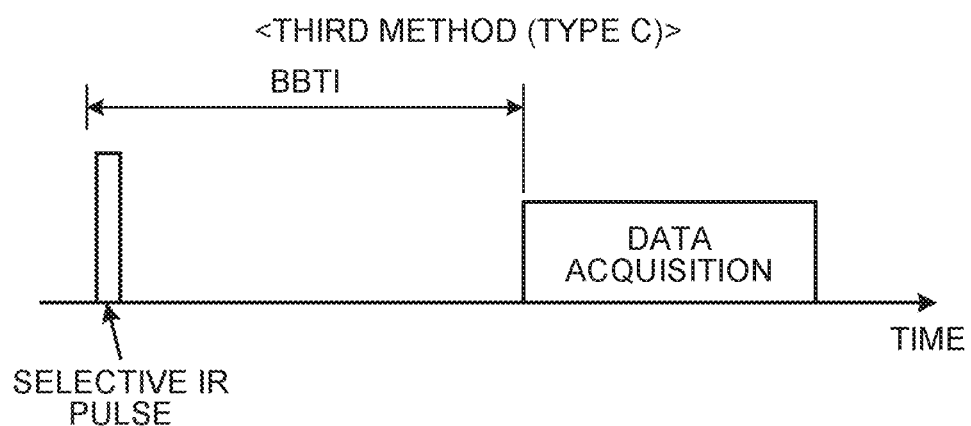
FIG. 5 illustrates a labeling method according to the embodiment.
Figure 6:
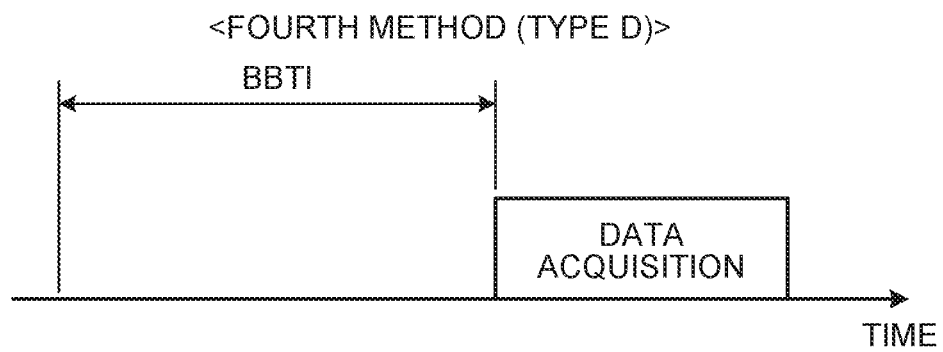
FIG. 6 illustrates a labeling method according to the embodiment.

If only a selective IR pulse is applied in an upstream region for the heart, then the blood signal is reversed (tagged) by a 180° nutation before traveling downstream into the heart tissue and the tagged blood pixels will be imaged as being dark compared to the background (FIG. 5, type C). By acquiring these three sets of image types (A, B, and C) within one breath-hold period to minimize registration errors, the myocardium can also be imaged by subtracting A from C because the signal from blood is the same for A and C, while the signal from myocardium is different between A and C. By applying a threshold operation, perfusion information in myocardium also can be extracted from the A and C image pair $$I_i = |A_i - B_i| F(|C_i - A_i|, T_{BBTI}) \quad (4)$$

in such a way that regions where blood flows into myocardium appear as being bright compared to the background.

The above image processing will be described more in detail. FIG. 10 illustrates the image processing of the embodiment. As indicated by "$C_i$−$A_i$" of Equation (4), the MRI data processor 42 performs a subtraction operation between a type-C labeled image and a type-A labeled image using complex numbers. As indicated by "|$C_i$−$A_i$|", the MRI data processor 42 then calculates the absolute value of the image based on the complex-valued subtraction operation. In the absolute value image, as FIG. 10(A) shows, the signal value of pixels for a region of myocardium is high (bright) and the signal value for other regions is low (bright).

The MRI data processor 42 performs a threshold operation on "|$A_i$−$B_i$|" using a function F. In an absolute value image of "|$A_i$−$B_i$|", as shown in FIG. 9(A), the signal value of pixels for a location where blood exists is high (bright) and the signal value of pixels for other locations is low (dark). Furthermore, the signal value of pixels of blood in locations excluding myocardium is high (bright). A masking operation to "|$A_i$−$B_i$|" using "|$C_i$−$A_i$|" generates an image shown in FIG. 10(B) where only pixels of blood in myocardium have a high signal value (bright).

The example where a type-A labeled image and a type-B labeled image are acquired in one breath-hold period and the example where a type-A labeled image, a type-B labeled image, and a type-C labeled image are acquired are describe above. However, embodiments are not limited to this. As described using Table 1, four types of labeling methods are available, depending on whether to use non-selective and/or selective IR pulses. It can be arbitrarily selected how many types of labeling methods or which types of labeling methods are combined. The MRI sequence controller 30 controls execution of pulse sequence such that labeled image based on the selected multiple types of (two to four) labeling methods can be acquired in one breath-hold period for one BBTI. The MRI sequence controller 30 may change multiple types of settings, e.g., increase PIF (Parallel Imaging Factor) of parallel imaging or reduce the number of slice encode or the number of slices. The MRI data processor 42 acquires desired images by, for example, appropriately performing a subtraction operation between labeled images that are acquired by the MRI sequence controller 30.

For example, the MRI system 100 may acquire desired images by performing the same calculations as Equations (1) to (3) using a combination of type C and type D instead of a combination of type A and type B. Because the background signal values are reduced for a combination of type A and type B, significant error will not be caused easily even if little misregistration remains. In contrast, a combination of type C and type D tends to cause significant error even with such little misregistration.

Image processing on type-A and type-B labeled images and image processing on type-A, type-B and type-C labeled images are not limited to the above-described examples. Threshold operations or inversion operations in the above-described processing may be appropriately omitted or added to acquire different desired images. It can be arbitrarily changed which types of images are acquired as desired images. Desired images can be changed depending on, for example, an object to be observed or whether the object is imaged brightly or darkly. To acquire such desired images, the MRI data processor 42 may perform necessary image processing using an arbitrary combination of necessary labeled images. In the above-described embodiment, a method of performing a subtraction operation between labeled images using complex numbers is described. However, this does not limit the scope of embodiments. For example, a subtraction operation between absolute value images may be performed.

Figure 11:
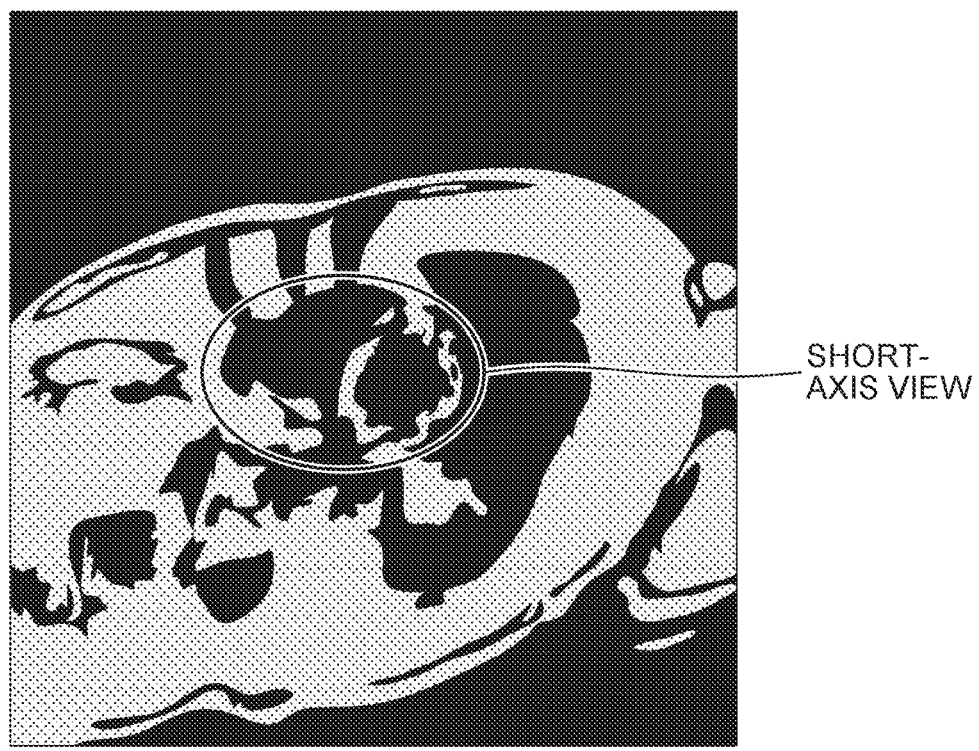
FIG. 11 is an exemplary display image that is generated in the embodiment.

The images created by Equation (1) normally do not image myocardium so brightly because the signal contribution from the myocardium is subtracted. This makes it difficult to see where the perfusion is taking place relative to myocardium tissue. To alleviate this situation, color image blending of a normal MRI image (of the same volume) registered with and blended with the type-A or type-B images is performed showing the exact location of blood flow relative to myocardium. Specifically, the MRI data processor 42 displays a display image that is generated by superimposing or compositing a labeled image and a processed image on which the above-described processing has been performed. FIG. 11 is an exemplary display image generated in the embodiment. The display image of FIG. 11 is obtained by superimposing a type-A (or type-B) labeled image displayed in black and white pixels on a processed image displayed in color pixels. Although FIG. 11 does not show, for example, a processed image in cyan is superimposed on a type-A labeled image that is displayed in black and white. The superimposition ratio (blending ratio for color image) can be changed appropriately. For example, a user can enhance the display of a labeled image or display of a processed image. The MRI data processor 42 may display a labeled image in color pixels and display a processed image in black and white pixels.

Figure 12:
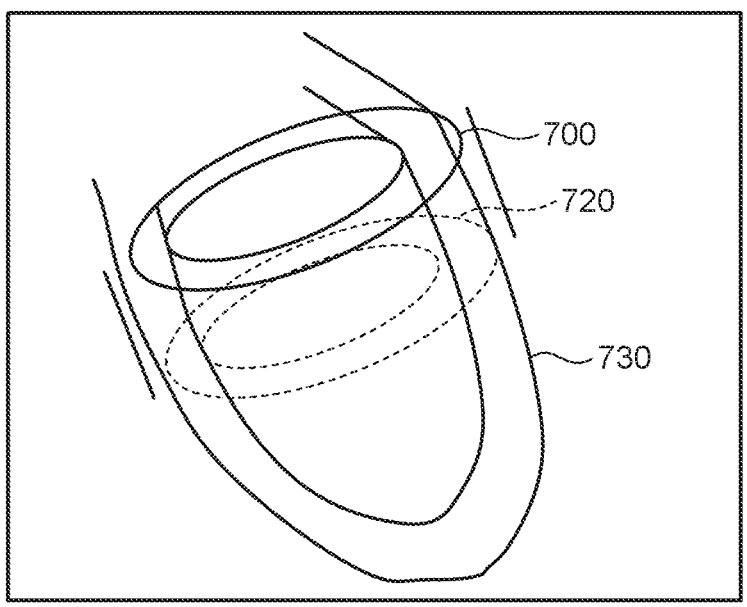
FIG. 12 depicts a volume rendering image according to the embodiment.

As described above, multi-slice data acquisitions with multiple types of BBTI values allow generation of a 4D data set that shows perfusion dynamics as a function of time, with BBTI as a time-dimensional control variable. 3D volume rendering makes it easy to view how blood flows into myocardium via coronary arteries from any viewing angle. Cine viewing allows the user to see blood perfusion as a function of BBTI (time). FIG. 12 is a sample picture of 3D volume rendering of processed slice images 700 to 720 on a 3D ventricle volume image 730.

Acquiring data with a wide range of BBTI values, for example, 100 msec to 2,000 msec with a 200 msec interval, allows calculation of mean transit time between blood entering the coronary arteries and blood dissipating in the myocardium. Plotting signal intensity as a function of BBTI at some sampling points makes it possible to see variations of the mean transit time over given locations.

By taking minimum intensity projection of all the images along the BBTI direction, regions of ischemic myocardium and/or myocardial infarct can be isolated as bright spots, which means that acquired signal did not change much between type A and type B over many BBTI values.

Figure 13:
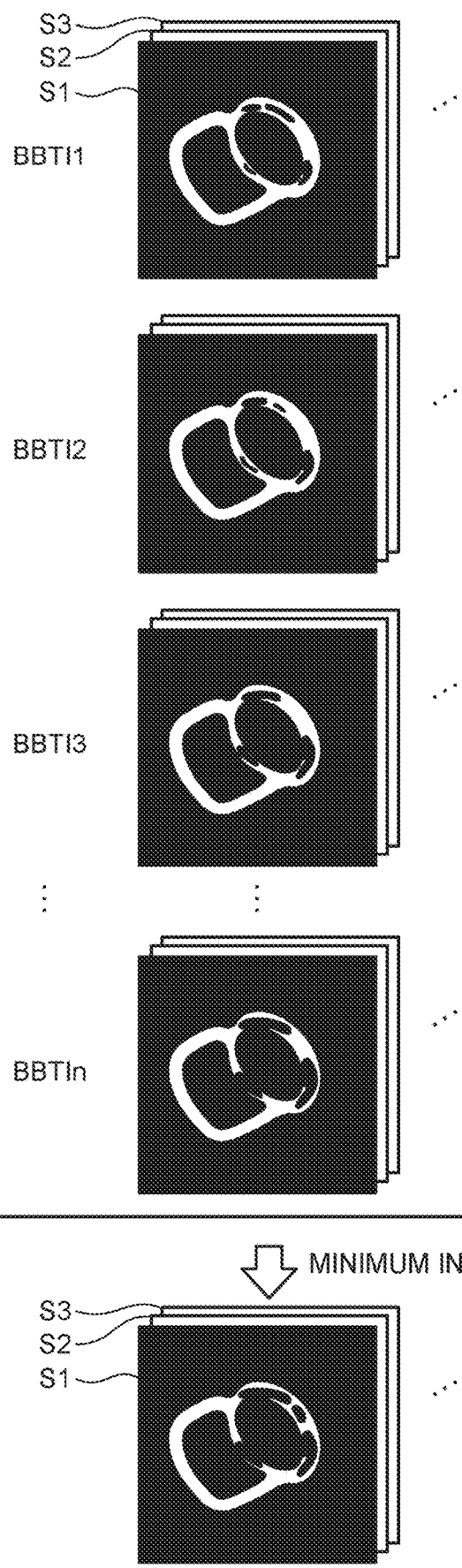
FIG. 13 illustrates minimum intensity projection along the BBTI direction.

This aspect will be described more in detail. FIG. 13 illustrates minimum intensity projection along the BBTI direction. For example, when the MRI sequence controller 30 acquires type-A and type-B volume data in one breath-hold period while changing the BBTI for each breath-hold period, the processed images on which the MRI data processor 42 has performed image processing are volume data for each BBTI, i.e., a 4D data set.

Because BBTI is the waiting time after application of a non-selective pulse until acquisition of MR signals is started, dynamics of blood which flows into the myocardium and perfuses appear in the group of time-series processed images of different BBTIs. As depicted in FIG. 13, for example, the state of blood appearing in each processed image of the processed image group of slices "S1" varies between BBTIs. In contrast, a region of ischemic myocardium or myocardial infarction corresponds to pixels for a location where blood has never existed (in processed images in any time phase) in the time-series processed image group.

The MRI data processor 42 performs minimum intensity projection along the BBTI direction for each slice of the processed image group. Specifically, the MRI data processor 42 generates projection images in a way that the MRI data processor 42 regards pixels of the time-series processed image group for a location where blood has existed even once as pixels having a low signal value, regards pixels of the processed image group for a location where blood has never existed as pixels having a high signal value. The pixels having a high signal value in an image where minimum intensity projection is performed are pixels for a location where blood has never existed however much BBTI has been changed, i.e., correspond to regions of ischemic myocardium and/or cardiac infarct. It is preferable that, when performing minimum intensity projection, the MRI data processor 42 perform known registration between processed images for different BBTIs.

By continuously reproducing slices of the processed image group chronologically, the MRI data processor 42 can display blood perfusion dynamics as cine views.

Type-A and type-B images are a minimum set of images that are preferably acquired within a single breath-hold period in order to obtain a registered processed image that shows areas with no bright blood flow. All three type-A, type-B and type-C images are preferably to be acquired within one breath-hold scan in order to obtain a different registered processed image (Equation (4)) that shows bright blood flow areas. It is preferred to acquire all images within one breath-hold period in order to avoid motion-related misregistration.

The preferred processing includes a combination of complex-valued subtraction operation, thresholding, reverse operation of image intensity and a masking operation by using the two types of images (A and B), the three types of images (A, B and C) or a different image combination.

The exemplary embodiment allows a single scan of 3D acquisitions using both first and second methods to reduce misregistration. The image process provides easy observation of marked blood entering into the myocardium.

The cardiac information on myocardium and blood perfusion through the coronary arteries can be more easily visualized and understood because:
  there is less misregistration of the interleaved type-A and type-B images;
  A versus B and/or A versus C image processing techniques provide clear depictions of perfusion;
  superimposition of a processed perfusion image using color blending of an original cardiac image adds contextual clarity to the perfusion image;
  3D volume rendering of processed perfusion images also adds contextual information to perfusion images; and/or
  data plotting can show signal intensity versus BBTI at sampling locations to better visualize blood perfusion mean transmit time.

Figure 14:
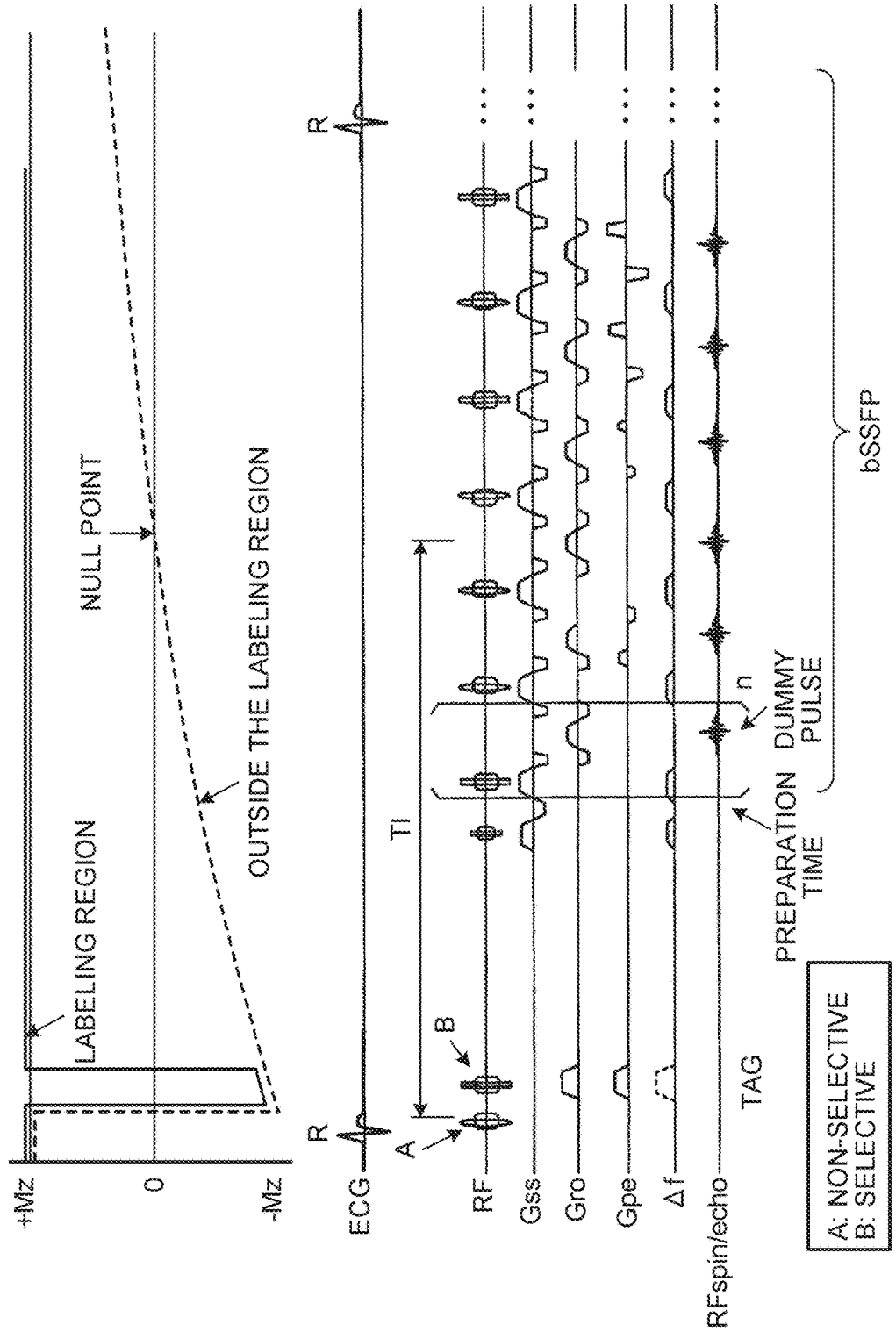
FIG. 14 depicts a sub-sequence according to the embodiment.
Figure 15:
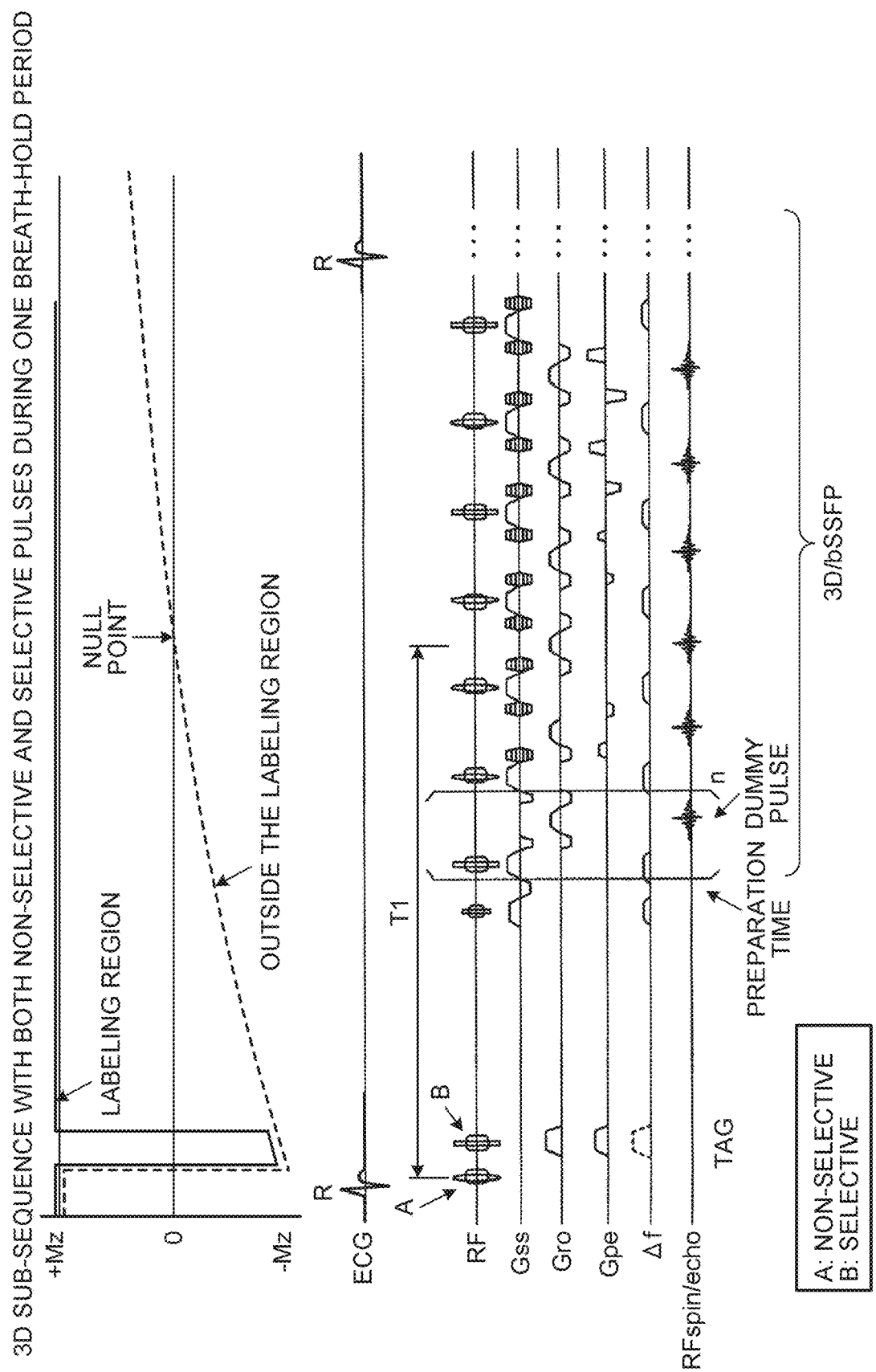
FIG. 15 depicts a sub-sequence according to the embodiment.

FIGS. 14 and 15 depicts a sub-sequence of the embodiment. FIGS. 14 and 15 depicts a sub-sequence of a labeling method (second method) where both of a non-selective IR pulse and a selective IR pulse are applied. As depicted in FIG. 14, a 2D sub-sequence of the second method can be used with both non-selective and selective IR pulses during one breath-hold period. A preparatory breath-hold instruction is issued to the patient (e.g., by a pre-agreed upon audible sound issued to the patient within the gantry while in the imaging position). The respiratory function of the patient (e.g., physical changes in chest cavity dimensions) could also typically be monitored thereafter to ensure that the patient actually does engage in one sustained breath-hold throughout the data acquisition sequence.

As depicted in FIG. 14, when the non-selective IR pulse A is applied, it substantially reverses the Z-axis +Mz magnetization of NMR (Nuclear Magnetic Resonance) nuclei to −Mz throughout the cardiac tissue of interest, including a labeled region. Thereafter, a selective IR pulse B is imposed on the region to be labeled, thus again reversing its magnetization (i.e., back to +Mz) so as to now be realigned in the positive Z-axis direction. However, NMR nuclei of the unlabeled region (including the region to be imaged) only recovers exponentially (in accordance with its T1 value) with the static magnetic field in the positive Z-axis direction. At some point, the region reaches a null point where there is effectively zero longitudinal magnetization in the unlabeled region (i.e., myocardium tissue to be imaged). While there is still a substantial difference in magnetization between blood that was in the labeled region (during application of the selective IR pulse B) and the cardiac myocardium (that was in the unlabeled region), imaging sub-sequences are effected for acquiring MRI data sufficient to generate at least one image of the myocardium tissue, e.g. a type-B image (image acquired when selective IR pulse is on), and at least one image of the myocardium tissue, e.g. a type A image (image acquired when selective IR pulse is off) during one breath-hold period. The exemplary MRI sequence depicted in FIG. 14 for data acquisition includes, for example, a conventional bSSFP. As will be appreciated, other known MRI data acquisition sequences may be employed. As will be explained in more detail below, preferably sub-sequences for gathering data on an image acquired when the selective IR pulse is on and an image acquired when the selective IR pulse is off will be interleaved with respect to time axis during an overall image data acquisition sequence during one breath-hold period.

FIG. 15 depicts that 3D phase encoding to acquire a volume of cardiac tissue. As those in the art will appreciate, 2D slice images can be utilized to acquire data for a multi-slice region or, alternatively, a 3D acquisition sequence may be utilized with additional phase encoding orthogonal to the slices so as to acquire, in one acquisition sequence, sufficient phase encoded data to image entire volume data if the captured data is subjected to appropriate 3D Fourier transformation.

Figure 16:
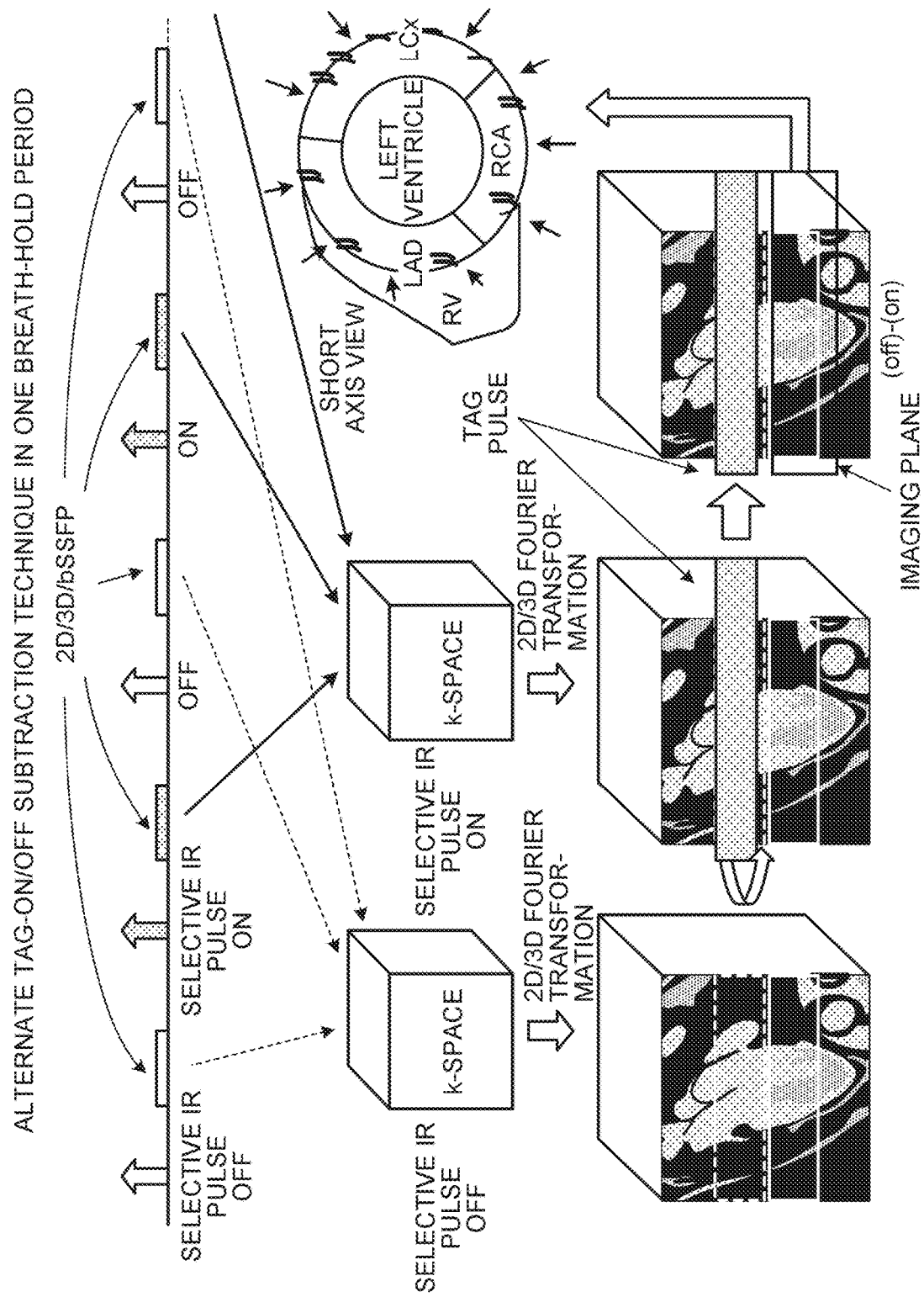
FIG. 16 depicts a data acquisition sub-sequence and an image processing technique.

FIG. 16 depicts the data acquisition sub-sequence and the image process technique of the embodiment. For example, the first excitation of the first method is followed by a first (2D or 3D bSSFP-type) data acquisition sub-sequence to partially acquire k-space data of a type-A image (acquired when selective IR pulse is off). Next, excitation using the second method occurs, followed by a corresponding data acquisition sub-sequence to partially acquire k-space data of, for example, a type-B image (acquired when selective IR pulse is off). This pattern is repeated as required to completely fill k-space for multi-slice images of selected volume. Once all of the data has been acquired (e.g. by interleaved data sub-sequence where partial data is acquired in one breath-hold period), a subtraction operation or thresholding is performed to subtract a type A image from a type B image (using complex-valued arithmetic) on a pixel-by-pixel basis so as to produce a "target" image of a myocardium tissue like the final output image depicted in FIG. 16 on the right side.

Figure 17:
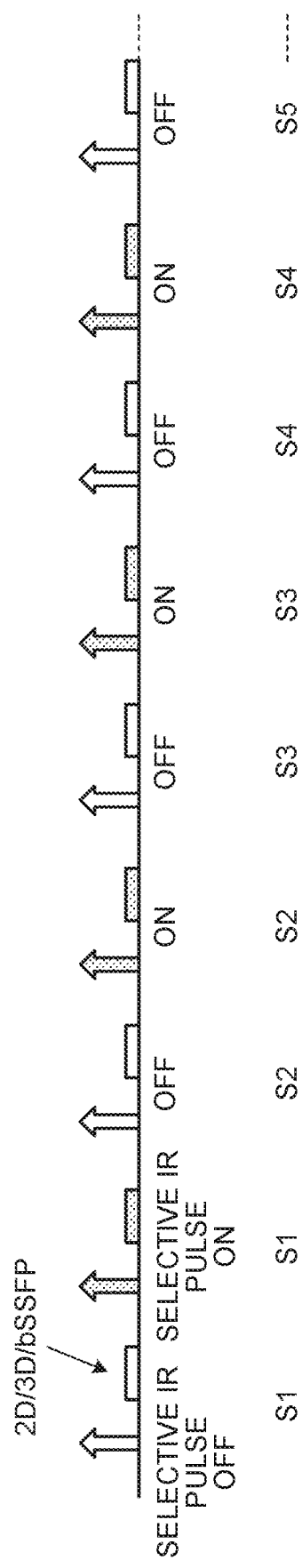
FIG. 17 depicts an alternate subsequence according to the embodiment.

FIG. 17 depicts the alternating interleaved sub-sequences to be employed within one breath-hold period for either 2D data acquisition or 3D data acquisition for coronary arteries of the myocardial tissue.

Figure 18:
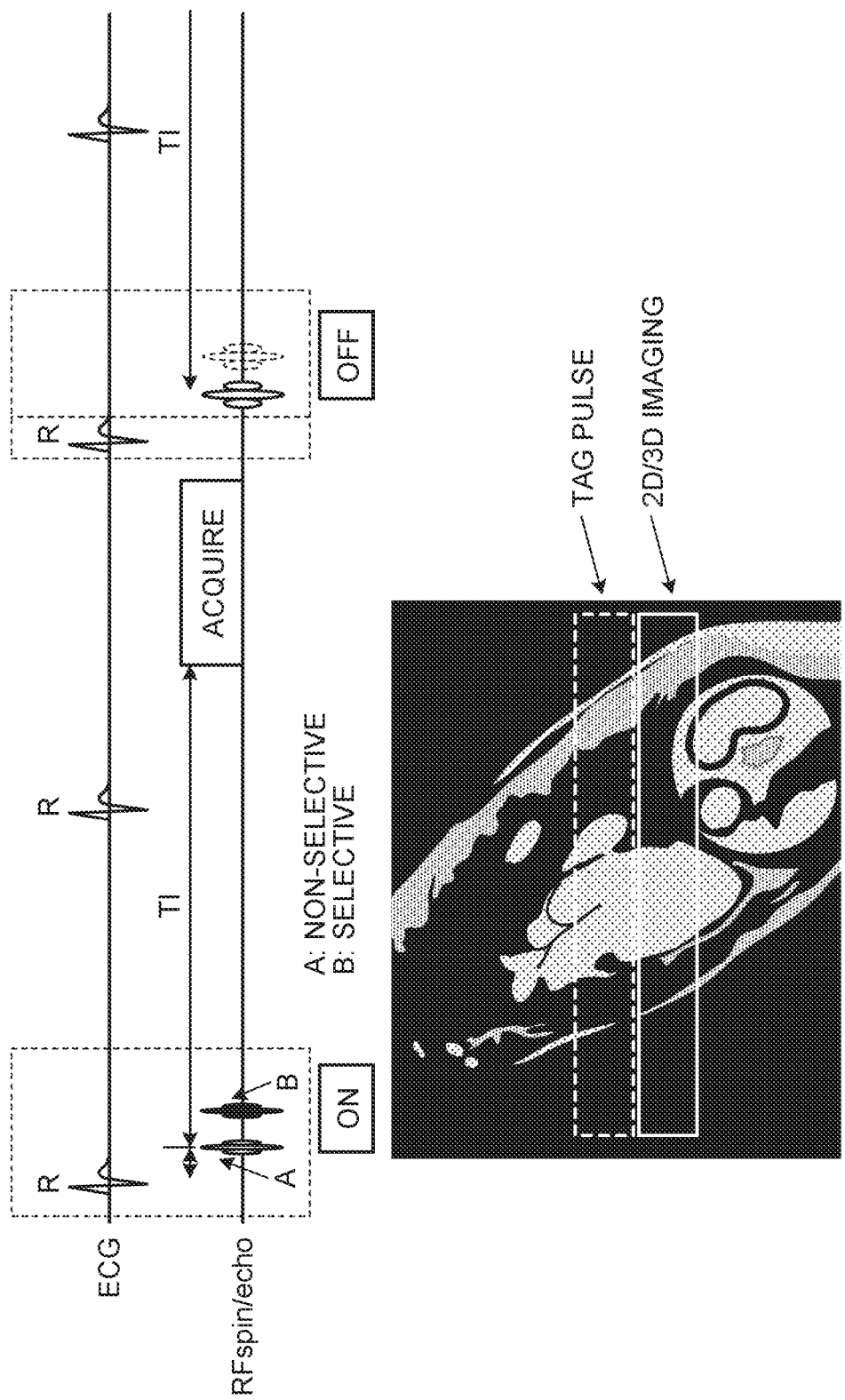
FIG. 18 shows an exemplary scout image (locator image) according to the embodiment.

FIG. 18 depicts a scout image (locator image) of the embodiment on which a labeled region (dotted line) and 2D/3D imaged area (solid line) are superimposed. FIG. 18 illustrates FIG. 18 shows a first sub-sequence from interleaved sub-sequences where a selective IR pulse is on and selective IR pulse is off. The first sub-sequence is shown so as to link with the ECG R-wave signal.

Figure 19:
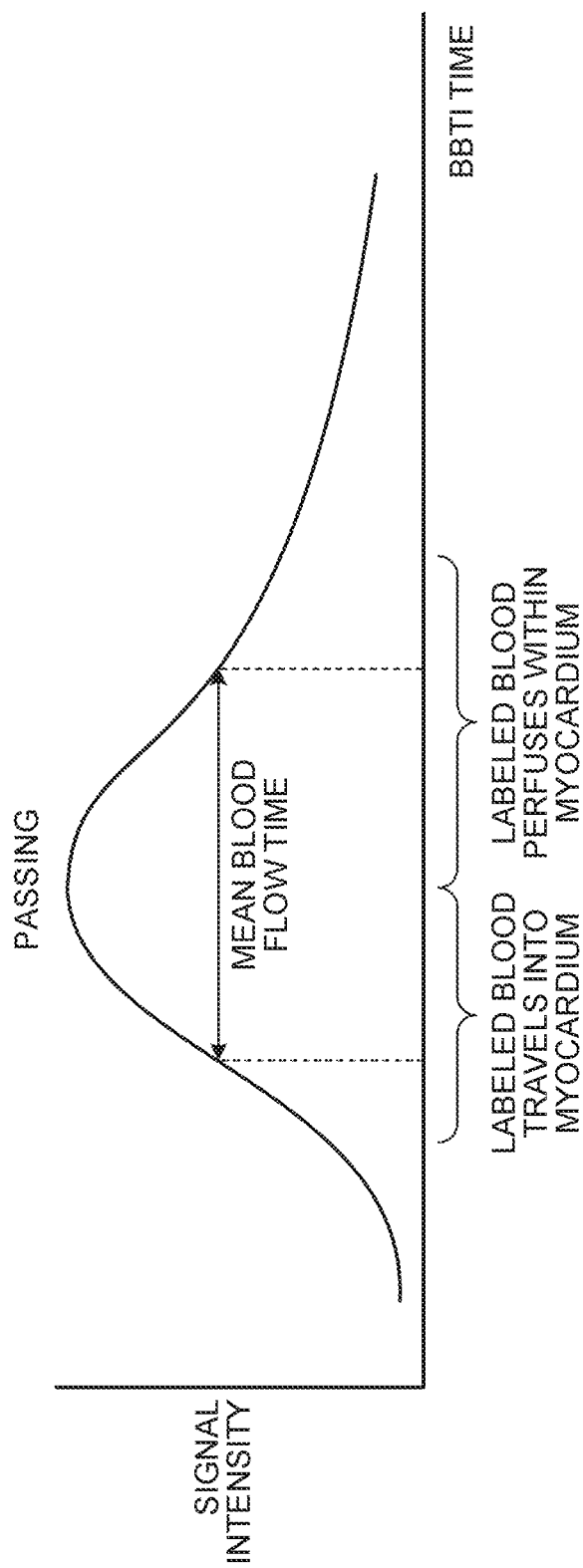
FIG. 19 is an exemplary plot representing image analysis result according to the embodiment.

FIG. 19 is an exemplary plot showing the result of image analysis according to the embodiment. FIG. 19 shows MRI signal intensity versus varied BBTI times. This plot demonstrates, for example, a bolus of labeled blood entering the heart arteries and thus building up towards a maximum as it enters—followed by reduced signal as the blood perfuses within the myocardium. The mean blood flow time for blood perfusion into the myocardium can then be calculated from such a plot as schematically depicted in FIG. 19.

This aspect will be described more in detail. Because a subtraction operation etc. are performed between multiple types of labeled images where misregistration is reduced according to the embodiment, processed images where the blood flowing or caused to flow into the myocardium is well imaged. By analyzing multiple types of labeled and processed images, the MRI data processor 42 acquires highly accurate cardiac information. For example, the MRI data processor 42 analyzes the signal intensity in myocardium with respect to above-described time-series processed image group. As shown in FIG. 19, as BBTI becomes longer, the blood signal intensity increases once. However, as the blood perfuses into the myocardium and dissipates, the signal intensity reduces. The MRI data processor 42 calculates, as the transit time (mean blood flow time) of the blood flowing in the myocardium, for example, FWHM (Full Width at Maximum) of the curve indicating the time-series change of such signal intensity. The MRI data processor 42 may display the curve indicating the time-series change of signal intensity as a plot on the display as shown in FIG. 19. It is preferable that sufficient range for calculating such time-series change is set as the BBTI range.

The image analysis by the MRI data processor 42 is not limited to this example. As described above, the MRI sequence controller 30 acquires multiple types of labeled images by executing a series of pulse sequences. The MRI data processor 42 may analyze multiple types of images depending on multiple types of labeled images captured images to acquire multiple types of analysis results.

Figure 20A:
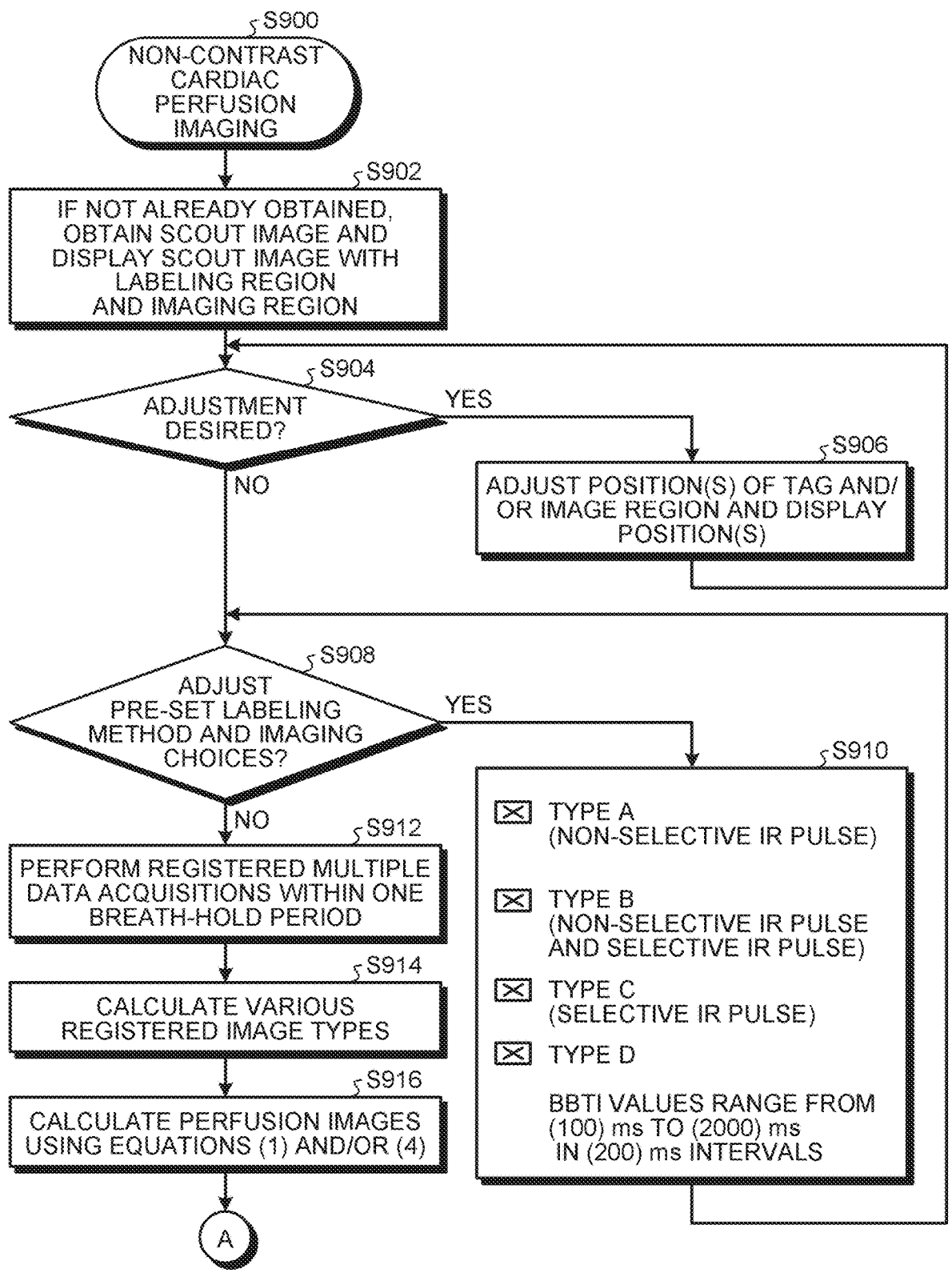
FIG. 20A provides a schematic illustration of a computer program code structure appropriate for the embodiment.
Figure 20B:
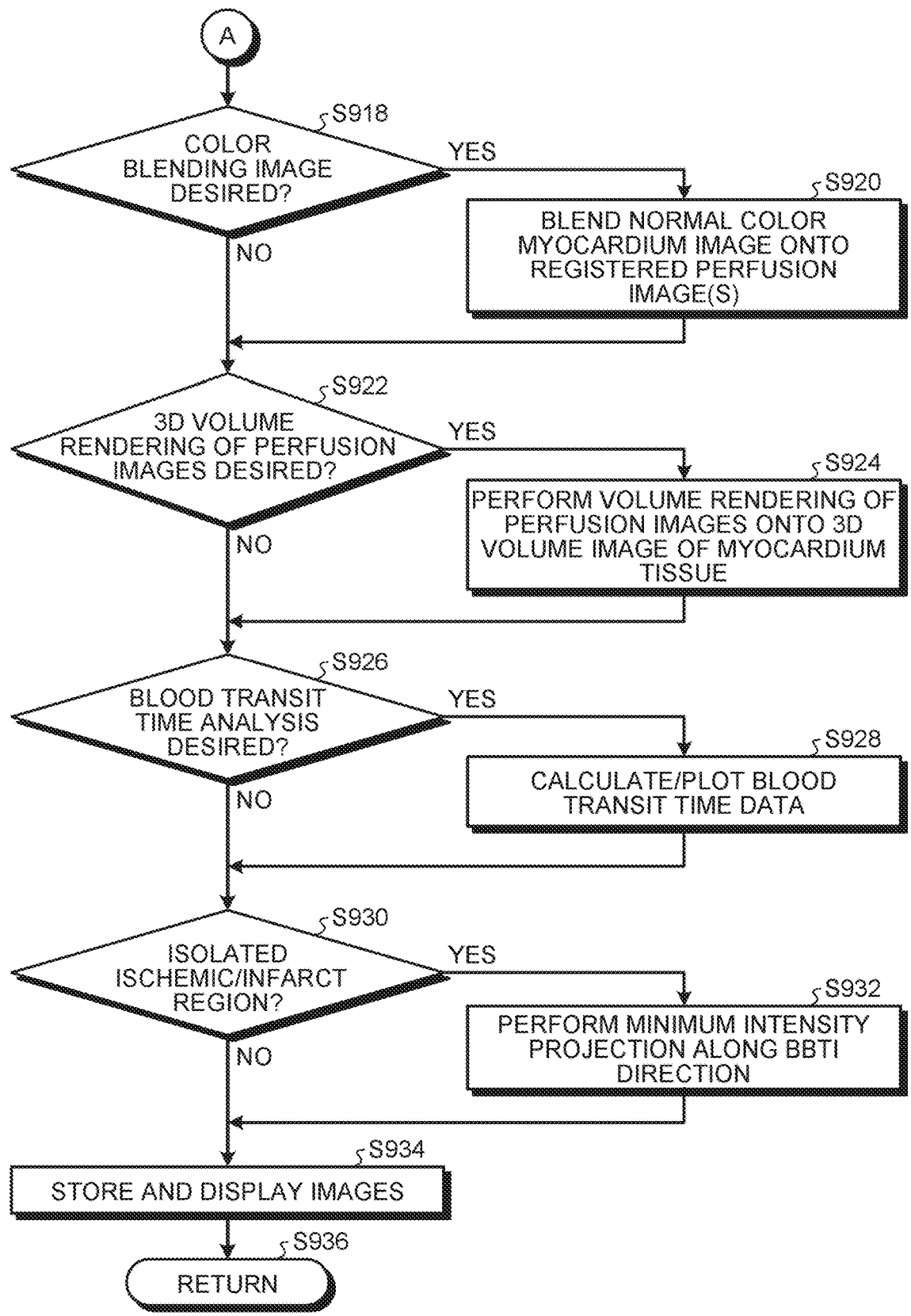
FIG. 20B provides a schematic illustration of a computer program code structure appropriate for the embodiment.

A schematic depiction of suitable computer program code structure for the embodiment is depicted at FIGS. 20A and 20B. Here, entry to a non-contrast cardiac perfusion imaging routine is made at step S900 (e.g., from an over-arching operating system or other MRI system control software). If a scout image (locator image) of the cardiac tissue has not already been obtained, the MRI system controller 22 obtains the scout image and then displays the scout image, along with a nominal labeled region and a region to be imaged (step S902) (e.g., such as depicted in the lower part of FIG. 18).

The operator is given an opportunity to adjust placement of the labeled region and imaged region (step S904). If adjustment desire is indicated (YES at step S904), then, the operator adjusts the positions of the labeling and/or imaged regions (step S906). Such adjusted positions are reflected in the scout images on the display. The MRI system controller 22 returns to step S904 to see if any further adjustment is desired. If not (NO at step S904), then the MRI system controller 22 passes to step S908. The operator is given an opportunity to adjust preset labeling and related imaging choices (step S908). If the operator elects to adjust such preset values (YES at step S908), the MRI system controller 22 passes to step S910 where, via the GUI (Graphical User Interface) shown in FIG. 20A, the operator is permitted choice of the types of labeling methods (sub-sequences) to be employed and the range of BBTI values in a Time-SLIP embodiment. As will be noted below, other sub-routine control parameters might also be entered at this point rather than providing separate operator choices at subsequent point (s) in the process.

Once the preset labeling and other related imaging choices have been made, then the MRI system controller 22 passes to step S912 where the MRI sequence controller 30 performs the preset multiple data acquisitions within one breath-hold. In particular, this provides, in accordance with the earlier explained exemplary embodiment, registered multiple data acquisitions for images to be further processed.

Once data has been acquired to fill k-space for at least one slice, the MRI data processor 42 uses the data to calculate labeled images (at step S914). The MRI data processor 42 generates hybrid perfusion images using predefined formulae such as Equation (1) and/or Equation (4) described above so as to calculate a difference between the calculated labeled images (step S916).

The operator is given a choice as to whether color blending of the resultant image is desired (step S918). If so (YES at step S918), the MRI data processor 42 accomplishes a blending between (a) a normal monochrome myocardium image (e.g., type A) and (b) a registered color-valued processed perfusion image (step S920). The operator is given a choice as to whether 3D volume rendering of perfusion images is desired (step S922). If so (YES at step S922), the MRI data processor 42 performs volume rendering of perfusion images (e.g., onto a 3D volume data of myocardium ventricular tissue) (step S924). The operator is given a choice as to whether blood transit time analysis is desired (step S926). If so (YES at step S926), the MRI data processor 42 calculates the blood transit time (e.g., possibly including a visualized and displayed plot of labeled blood signal intensity versus BBTI time as in FIG. 19) (step S928).

The operator is given a choice as to whether it is desired to generate a display that can isolate ischemic myocardium and/or myocardial infarct regions of the imaged myocardium (step S930). If so (YES at step S930), the MRI data processor 42 performs a minimum intensity projection over perfusion images for different BBTI so as to result in an image that shows a "bright" region where there has been little change in signal intensity over a fairly large number of BBTI values (step S932).

The MRI data processor 42 may store all or some of the generated images or display them to the operator (step 5934) before a return is effected at 5936 to the calling system.

Other Embodiments

The embodiments described above does not limit the scope of embodiments.

Specific Values and Procedures

The specific values and procedures of the above-described embodiments have been presented by way of example only. For example, an exemplary procedure has been described using FIGS. 20A and 20B but it does not limit the scope of embodiments and it can be changed as required depending on the operation mode. The order of processes depicted in FIGS. 20A and 20B can be changed arbitrarily. For example, color blending, volume rendering, blood transit time analysis, isolation of ischemic myocardium and/or regions of myocardial infarction may be performed in an arbitrary order or performed individually. Each of the processes in the procedure depicted in FIGS. 20A and 20B may be selected appropriately or omitted. FIGS. 20A and 20B depict an example where displaying of scout images, setting of labeling method, execution of sub-sequences and the following image processing and image analysis are performed as a series of processes. However, this does not limit the scope of embodiments. For example, processes from display of scout images to execution of pulse sequences may be performed as a series of processes and following image processing and image analysis may be performed as post processing separately from data acquisition.

Trigger Signal

In the above-described embodiment, an electrocardiogram signal is used as a trigger signal such that data is acquired in synchronization with electrocardiogram. However, this does not limit the scope of embodiments. Instead of electrocardiogram signals, other biosignals, such as pulse wave signals or respiratory signals, or clock signals of the MRI system 100 may be used as trigger signals.

Image Processing Apparatus

An exemplary embodiment is described above where the MRI system 100 performs all of data acquisition, image processing and image analysis, but this does not limit the scope of embodiments. For example, an image processing system including the MRI system 100 and an image processing apparatus may perform above-described multiple types of processes. Here, the image processing apparatus can be various apparatuses such as a work station, an image memory device (image server) and a viewer of a PACS (Picture Archiving and Communication System), or an electronic medical record system. For example, the MRI sequence controller 30 of the MRI system 100 acquires data while the image processing apparatus receives, via a network, the acquired MR data or k-space data from the MRI system 100 or an image server or receives such data that is input by an operator using a recording medium and stores the data in a memory. The image processing apparatus may perform various types of processing (e.g., processing performed by the MRI data processor 42) on the MR data or k-space data that is stored in the memory.

Labeling Pulse

In the above-described embodiment, IR pulses are used as labeling pulses. However, this does not limit the scope of embodiments. Other pulses such as SAT (saturation) pulses, SPAMM (Spatial Modulation Of Magnetization) pulses or DANTE pulses may be used as labeling pulses.

Region of Interest

The exemplary embodiment is described above where the heart is supposed to be a region of interest and a blood vessel image where blood flowing into myocardium is imaged. However, this does not limit the scope of embodiments. The region of interest may be a different region such as lever or kidney. Furthermore, object to be labeled is not limited to blood. It may be CSF (Cerebrospinal Fluid), pancreatic fluid or lymph fluid.

Breath-Hold

The exemplary embodiment is described above where a pulse sequence is executed in one breath-hold using a combination of multiple types of labeling methods. However, this does not limit the scope of embodiments. The MRI sequence controller 30 may combine, regardless whether there is a breath-hold, multiple types of labeling methods over a series of successive pulse sequences without waiting time (e.g., without input operation by the user) to acquire multiple types of labeled images.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging (MRI) apparatus comprising:
    a sequence controller configured to execute a non-contrast pulse sequence using a combination of multiple types of non-contrast labeling methods to acquire magnetic resonance (MR) signals to obtain cardiac information representing blood flow within myocardium, the multiple types of labeling methods including a first labeling method and a second labeling method; and
    a data processor configured to generate multiple types of labeled MR images based on the magnetic resonance signals, the multiple types of labeled MR images including a first MR image A obtained from the first labeling method and a second MR image B obtained from the second labeling method,
    wherein the data processor is configured to generate an image C having pixel values based on a product of
    (a) pixel values obtained from a difference between respectively corresponding pixels of the first and second images so as to provide pixel values that (1) are representing blood flow while suppressing pixel values representing myocardium and (2) are obtained from a reverse intensity operation, the reverse intensity operation being an operation such that pixels become depicted brighter as the difference becomes smaller, and
    (b) pixel values obtained from a larger value of respectively corresponding pixels of the first and second images so as to provide pixel values representing blood flow and not myocardium,
    the resulting image C providing an enhanced image of blood flow.

2. The MRI apparatus according to claim 1, wherein the multiple types of labeling methods include at least two methods from a first method in which a labeling pulse is applied without a region being selected, a second method in which a labeling pulse which is applied with a region being selected and a labeling pulse which is applied without a region being selected are applied; a third method in which a labeling pulse is applied to a selected region, and a fourth method in which no labeling pulse is applied.

3. The MRI apparatus according to claim 1, wherein the sequence controller executes a pulse sequence using a combination of the multiple types of labeling methods to acquire magnetic resonance signals corresponding to multiple types of volume data or multiple types of multi-slice data in one breath-hold period.

4. The MRI apparatus according to claim 3, wherein the sequence controller acquires magnetic resonance signals while changing, in each breath-hold time, a waiting time after application of a labeling pulse until acquisition of magnetic resonance signals is started.

5. An image processing apparatus comprising:
    a memory configured to store magnetic resonance (MR) signals that are acquired by executing a non-contrast magnetic resonance imaging (MRI) pulse sequence using a combination of multiple types of labeling methods, the non-contrast MRI pulse sequence using a first labeling method and a second labeling method; and
    a data processor configured to generate multiple types of labeled MR images based on the magnetic resonance signals, the multiple types of labeled images including a first MR image A obtained from the first labeling method and a second MR image B obtained from the second labeling method, and the data processor is configured to generate an image C based on a product of
    (a) pixel values obtained from a difference between respectively corresponding pixels of the first and second images so as to provide pixel values that (1) are representing blood flow while suppressing pixel values representing myocardium and (2) are obtained from a reverse intensity operation, the reverse intensity operation being an operation such that pixels become depicted brighter as the difference becomes smaller, and (b) pixel values obtained from a larger value of respectively corresponding pixels of the first and second images so as to provide pixel values representing blood flow and not myocardium, the resulting image C providing an enhanced image of blood flow.

6. The image processing apparatus according to claim 5, wherein the data processor generates a subtraction image by performing a subtraction operation using complex numbers between the multiple types of labeled images.

7. The image processing apparatus according to claim 5, wherein
the first labeling method is a method in which a labeling pulse is applied without a region being selected and the second labeling method is a method in which a labeling pulse which is applied with a region being selected and a labeling pulse which is applied without a region being selected are applied, and
the data processor performs a subtraction operation using complex numbers between the first image and the second image and performs a reverse operation on an absolute value image acquired by performing the subtraction operation to show, in high signal values, pixels for a region where no blood exists.

8. An image processing apparatus comprising:
a memory configured to store magnetic resonance signals that are acquired by executing a non-contrast pulse sequence using a combination of multiple types of non-contrast labeling methods; and
a data processor configured to generate multiple types of labeled images A, B, and C based on the magnetic resonance signals and configured to generate a subtraction image by performing a subtraction operation between respectively corresponding pixel values of the multiple types of labeled images, wherein
the multiple types of labeling methods are a first method in which a labeling pulse is applied without a region being selected to provide image A, a second method in which a labeling pulse which is applied with a region being selected and a labeling pulse which is applied without a region being selected are applied to provide image B, and a third method in which a labeling pulse is applied to a selected region to provide image C,
the first method being a method in which the labeling pulse is applied without the region being selected and data acquisition is performed at a null point where there is zero longitudinal magnetization, the second method being a method in which the labeling pulse which is applied with the region being selected and the labeling pulse which is applied without the region being selected are applied and data acquisition is performed at the null point, and the third method being a method in which the labeling pulse is applied to the selected region and data acquisition is performed at the null point, and
the data processor masks a first absolute value image with a second absolute value image, the first absolute value image being acquired by performing the subtraction operation using complex numbers between respectively corresponding pixels of image A and image B, the second absolute-value image being acquired by performing the subtraction operation using complex numbers between respectively corresponding pixels of image A and image C in accordance with the following formula for pixel value at an ith pixel location: $I_i=|A_i-B_i|F(|C_i-A_i|, T_{BBTI})$, wherein the $T_{BBTI}$ is BBTI(Black Blood Time to Inversion) and the F is a continuous function and a function of the BBTI.

9. The image processing apparatus according to claim 5, wherein
the magnetic resonance signals are acquired while changing a waiting time after application of a labeling pulse until acquisition of magnetic resonance signals is started, and
the data processor generates a subtraction image for each waiting time by performing a subtraction operation between multiple types of labeled images corresponding to the same waiting time.

10. The image processing apparatus according to claim 9, wherein
the magnetic resonance signals are acquired for a heart, and
the data processor generates a myocardium perfusion image as the subtraction image for each waiting time.

11. The image processing apparatus according to claim 9, wherein the data processor projects a signal value of the subtraction image along a waiting time direction.

12. The image processing apparatus according to claim 5, wherein the data processor generates a display image obtained by a superposition of or a composition of the multiple types of labeled images and the processed image on which image processing including a subtraction operation between the multiple types of labeled images has been performed.

13. An image processing apparatus comprising:
a memory configured to store magnetic resonance (MR) signals that are acquired by executing a non-contrast magnetic resonance imaging (MRI) pulse sequence using a combination of multiple types of non-contrast labeling methods, the multiple types of labeling methods including a first labeling method and a second labeling method; and
a data processor configured to generate multiple types of labeled MR images based on the magnetic resonance signals, the multiple types of labeled images including a first MR image A obtained from the first labeling method and a second MR image B obtained from the second labeling method, and configured to perform an analysis using the multiple types of labeled images and generate an image C based on a product of
(a) pixel values obtained from a difference between respectively corresponding pixels of the first and second images so as to provide pixel values that (1) are representing blood flow while suppressing pixel values representing myocardium and (2) are obtained from a reverse intensity operation, the reverse intensity operation being an operation such that pixels become depicted brighter as the difference becomes smaller, and
(b) pixel values obtained from a larger value of respectively corresponding pixels of the first and second images so as to provide pixel values representing blood flow and not myocardium,
the resulting image C providing an enhanced image of blood flow.

14. The image processing apparatus according to claim 13, wherein
the magnetic resonance signals are acquired while changing a waiting time after application of a labeling pulse until acquisition of magnetic resonance signals is started, and
the data processor generates a subtraction image for each waiting time by performing a subtraction operation between multiple types of labeled images corresponding to the same waiting time and analyzes a signal intensity of a generated time-series subtraction image group.

15. The image processing apparatus according to claim 14, wherein
the magnetic resonance signals are acquired for a heart, and
the data processor analyzes the signal intensity of the subtraction image group to calculate a transit time of blood entering the myocardium of the heart.

16. The image processing apparatus according to claim 14, wherein the data processor plots a result of analyzing the signal intensity of the subtraction image group and displays the plot on a display unit.

17. The image processing apparatus according to claim 13, wherein the data processor uses the multiple types of labeled images to perform multiple types of analysis appropriate for the respective labeled images.

\* \* \* \* \*